United States Patent
Shi et al.

(10) Patent No.: US 7,714,187 B2
(45) Date of Patent: May 11, 2010

(54) PHYTATE POLYNUCLEOTIDES AND METHODS OF USE

(75) Inventors: Jinrui Shi, Johnston, IA (US); Heidi G. Major Sleister, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 109 days.

(21) Appl. No.: 11/054,168

(22) Filed: Feb. 9, 2005

(65) Prior Publication Data

US 2005/0273879 A1    Dec. 8, 2005

Related U.S. Application Data

(60) Provisional application No. 60/543,079, filed on Feb. 9, 2004.

(51) Int. Cl.
*C12N 15/82* (2006.01)
*A01H 5/00* (2006.01)
*A01H 5/10* (2006.01)

(52) U.S. Cl. ............... 800/285; 800/278; 800/298; 800/320.1

(58) Field of Classification Search ............... 536/23.1, 536/23.6; 435/320.1; 800/278, 285, 298, 800/320.1
See application file for complete search history.

(56) References Cited

U.S. PATENT DOCUMENTS

| 2003/0175965 | A1 | 9/2003 | Lowe et al. | |
| 2004/0034888 | A1* | 2/2004 | Liu et al. | 800/289 |
| 2004/0214272 | A1* | 10/2004 | La Rosa et al. | 435/69.1 |

FOREIGN PATENT DOCUMENTS

| WO | WO 98/45448 | * | 10/1998 |
| WO | WO 99/05298 A1 | | 2/1999 |
| WO | WO 99/55879 A1 | | 11/1999 |
| WO | WO 03/027243 A2 | | 4/2003 |
| WO | WO 05/014794 A2 | | 2/2005 |

OTHER PUBLICATIONS

Gutterson (1995, HortScience 30(5):964-966).*
Emery et al (2003, Current Biology 13:1768-1774).*
Bowie et al, Science 247:1306-1310, 1990.*
McConnell et al, Nature 411 (6838):709-713, 2001.*
Nunes et al (2006, Planta 224:125-132).*
Chuang et al (2000, PNAS 97(9):4985-4990).*
EMBL Database Report for Accession No. Q7XQZ6, Oct. 1, 2003 (XP002333656).
Abbott, J.C., et al., "Simultaneous Suppression of Multiple Genes by Single Transgenes. Down-Regulation of Three Unrelated Lignin Biosynthetic Genes in Tobacco," *Plant Phys.*, Mar. 2002, pp. 844-854, vol. 128.
Chuang, C-F and E. M. Meyerowitz, "Specific and Heritable Genetic Interference by Double-Stranded RNA in *Arabidopsis thaliana*," *PNAS*, Apr. 25, 2000, pp. 4985-4990, vol. 97, No. 9.
Ives, E.B., et al., "Biochemical and Functional Characterization of Inositol 1, 3, 4, 5, 6-Pentakisphosphate 2-Kinases," *J. Biol. Chem.*, Nov. 24, 2000, pp. 36575-36583, vol. 275, No. 47.
Phillippy, B.Q., et al., "Purification and Some Properties of Inositol 1, 2, 4, 5, 6-Pentakisphosphate 2-Kinase from Immature Soybean Seeds," *J. Biol. Chem.*, Nov. 11, 1994, pp. 28393-28399, vol. 269, No. 45.
Pandolfini, T., et al., "Expression of Self-Complementary Hairpin RNA Under the Control of the rolC Promoter Confers Systemic Disease Resistance to Plum Pox Virus Without Preventing Local Infection," *BMC Biotechnology*, Jun. 25, 2003, pp. 1-15, vol. 3, No. 7.
Stoutjesdijk, P. A., "phRNA-Mediated Targeting of the Arabidopsis FAD2 Gene Gives Highly Efficient and Stable Silencing," *Plant Phys.*, Aug. 2002, pp. 1723-1731, vol. 129.
Verbsky, J.W., "The Synthesis of Inositol Hexakisphosphate," *J. Biol. Chem.*, Aug. 30, 2002, pp. 31857-31862, vol. 277, No. 35.
Waterhouse, P.M. And C. A. Helliwell, "Exploring Plant Genomes by RNA-Induced Gene Silencing," *Nat. Rev. Gen*, Jan. 2003, pp. 29-38, vol. 4.
Genbank Database Accession No. AL606608, Direct Submission, Sep. 8, 2001.
Genbank Database Accession No. AK102842, Direct Submission, Aug. 27, 2002.
Genbank Database Accession No. AY104429, Direct Submission Apr. 25, 2002.
Genbank Database Accession No. AY111282, Direct Submission Apr. 25, 2002.
Genbank Database Accession No. BT017356, Direct Submission Oct. 27, 2004.
Genbank Database Accession No. XM_474214, Direct Submission Jul. 1, 2004.

* cited by examiner

*Primary Examiner*—Stuart F. Baum
(74) *Attorney, Agent, or Firm*—Alston & Bird LLP

(57) ABSTRACT

Compositions and methods are provided for modulating the level of phytate in plants. More specifically, the invention relates to methods of modulating the level of phytate utilizing nucleic acids comprising Ins (1,3,4,5,6)$P_5$2-kinase (IP2K) nucleotide sequences to modulate the expression of IP2K in a plant of interest. The compositions and methods of the invention find use in agriculture for improving the nutritional quality of food and feed by reducing the levels of phytate and/or increasing the levels of non-phytate phosphorus in food and feed. The invention also finds use in reducing the environmental impact of animal waste.

5 Claims, 7 Drawing Sheets

FIGURE 3A

```
                              401                                                                          450                                                             500
    Zea mays IP2K-1  (291) RSEVLGNLLATQKLDDHDIEGVIHEYNELSQPCLVCKNLTDVELLRKVTFLHSLPLDKSEKIVRDFLISATAKDCSLMISFRPR-ENGSTDSEYDSVFL
    Zea mays IP2K-2  (377) KSGVLGKLLTTQKLDDHDIEGAIHLYNMLSQPCLVCKNLTDVELLRKVTLLHSLPLDKSEKIVRNFLISATAKDCSLMISFRPR-ENGSTDSEYDSVFL
          At5g42810  (297) GSGVLDRLLEIQKLDKLDIEGAIHSYDDLNQPCPICKEGKP---LEAELSLHALPLDESLKIVKEYLIAATAKDCSIMISFQSRNAWDSEPS-GDYVSL
          At1g22100  (312) TSGVLDQLLDVQKLDRNNIEGAIHNYDFIDQPCKVCREEN------QESMHSTPMDEKVNIEKEFLISATAKDCSVMISFRSTEAGLSKSSSHSNEHL
Brassica IP2K N-terminal  (289) ------------------------------------------------------------------------------------------------
    Rice protein    (289) KSGVLGKLLATQKLDDHDIEGAIHEYNMLSQPCLVCKSETDTELLRKYSTLHSLPLDKSEKIVRDFLISATAKDCSLMISFRPR-QSGTDSEYDSVFL
         Consensus (401)   SGVL LL  QKLD HDIEGAIHLYY II QPC VCK L    L  YS LHSLPLD SLKIVRDFLISATAKDCSLMISFR R     S   S YD V L 501                                                      550
    Zea mays IP2K-1  (390) ESVKRRVEYKAYFDDLDVKPLDKMEHYEKLDQRIVNFYTRNG----GGLAISKGQ----
    Zea mays IP2K-2  (476) ESAKRRVEYKTYFVDLDVKPLDKMVHYEKLDQRIVNSYTRYG----EVLPPPKGK----
          At5g42810  (393) KPTNQFEDYKVHFEDLSEKPLKRMESYKKLDKKIESFYNRKQKAENTAEQIGNSKPSHS
          At1g22100  (406) ELTKQEREYKVHFDDLDMRPLKKMEVYELDKKIMNTYLEMLKKKGTQPQCL-------
Brassica IP2K N-terminal  (289) ----------------------------------------------------------
    Rice protein    (388) DSVNQSXDYKAYFDDLNKPLDKMVHYEKLDQKIVNFYTRNGEVGGDPRDPPKGCGPR-
         Consensus (501)   ES    TYEYK YFIDLDVKPL KM  YFFKLD KIVN Y R
```

FIGURE 3B

PHP20588
2940 bp

PHP21330
5303 bp

PHP21334
7916 bp

PHYTATE POLYNUCLEOTIDES AND METHODS OF USE

CROSS-REFERENCE TO RELATED APPLICATIONS

This application claims the benefit of U.S. Provisional Application No. 60/543,079, filed Feb. 9, 2004; the contents of which application is herein incorporated by reference in its entirety.

FIELD OF THE INVENTION

The present invention relates to the field of animal nutrition. Specifically, the present invention relates to the identification and use of genes encoding enzymes involved in the metabolism of phytate in plants and the use of these genes and mutants thereof to reduce the levels of phytate, and/or increase the levels of non-phytate phosphorus in food or feed.

BACKGROUND OF THE INVENTION

The role of phosphorous in animal nutrition is well recognized. Phosphorus is a critical component of the skeleton, nucleic acids, cell membranes and some vitamins. Though phosphorous is essential for the health of animals, not all phosphorous in feed is bioavailable.

Phytates are the major form of phosphorous in seeds. For example, phytate represents about 60-80% of total phosphorous in corn and soybean. When seed-based diets are fed to non-ruminants, the consumed phytic acid forms salts with several important mineral nutrients, such as potassium, calcium, and iron, and also binds proteins in the intestinal tract. These phytate complexes cannot be metabolized by monogastric animals and are excreted, effectively acting as anti-nutritional factors by reducing the bioavailability of dietary phosphorous and minerals. Phytate-bound phosphorous in animal excreta also has a negative environmental impact, contributing to surface and ground water pollution.

There have been two major approaches to reducing the negative nutritional and environmental impacts of phytate in seed. The first involves post-harvest interventions, which increase the cost and processing time of feed. Post-harvest processing technologies remove phytic acid by fermentation or by the addition of compounds, such as phytases.

The second is a genetic approach. One genetic approach involves developing crop germplasm with heritable reductions in seed phytic acid. While some variability for phytic acid was observed, there was no change in non-phytate phosphorous. Further, only 2% of the observed variation in phytic acid was heritable, whereas 98% of the variation was attributed to environmental factors.

Another genetic approach involves selecting low phytate lines from a mutagenized population to produce germplasm. Most mutant lines exhibit a loss of function and are presumably blocked in the phytic acid biosynthetic pathway; therefore, low phytic acid accumulation will likely be a recessive trait. In certain cases, this approach has revealed that homozygosity for substantially reduced phytate can be lethal.

Another genetic approach is transgenic technology, which has been used to increase phytase levels in plants. These transgenic plant tissues or seed have been used as dietary supplements.

The biosynthetic route leading to phytate is complex and not completely understood. Without wishing to be bound by any particular theory of the formation of phytate, it is believed that the synthesis may be mediated by a series of one or more ADP-phosphotransferases, ATP-dependent kinases, and isomerases. A number of intermediates have been isolated, including, for example, monophosphates such as D-myo-inositol 3-monophosphate, diphosphates ($IP_2$s) such as D-myo-inositol 3,4-bisphosphate, trisphosphates ($IP_3$s) such as D-myo-inositol 3,4,6 trisphosphate, tetraphosphates ($IP_4$s) such as D-myo-inositol 3,4,5,6-tetrakisphosphates, and pentaphosphates ($IP_5$s) such as D-myo-inositol 1,3,4,5,6-pentakisphosphate. The phosphorylation of the $IP_5$ to $IP_6$ is found to be reversible. Several futile cycles of dephosphorylation and rephosphorylation of the $IP_5$ and $IP_6$ forms have been reported as well as a cycle involving glucose-6-phosphate->D-myo-inositol 3-monophosphate->myo-inositol, the last step being completely reversible. The reversibility of this step suggests that control of metabolic flux through this pathway may be important.

Based on the foregoing, there exists the need to improve the nutritional content of plants, particularly corn and soybean, by increasing non-phytate phosphorous and reducing seed phytate. Ins(1,3,4,5,6)$P_5$ 2-kinases ("IP2Ks") are responsible for the last step of phytic acid biosynthesis. Accordingly, it is desirable to modulate the expression of IP2Ks to reduce seed phytate and to increase non-phytate phosphorus.

SUMMARY OF THE INVENTION

Compositions and methods are provided for modulating the level of phytate in plants. More specifically, the invention relates to methods of modulating the level of phytate utilizing Ins (1,3,4,5,6)$P_5$2-kinase ("IP2K") nucleic acids to produce transformed plants that exhibit decreased IP2K expression. The compositions and methods of the invention find use in agriculture for improving the nutritional quality of food and feed by reducing the levels of phytate and/or increasing the levels of non-phytate phosphorus in food and feed. The invention also finds use in reducing the environmental impact of animal waste. Also provided are compositions and methods for producing IP2K proteins.

BRIEF DESCRIPTION OF THE DRAWINGS

FIGS. 3A and 3B shows an alignment of two maize IP2Ks with other plant proteins. Shading indicates amino acids that support the consensus sequence. Five conserved domains were revealed, as diagrammed in FIG. 4. The sequences aligned included two novel maize IP2K proteins set forth in SEQ ID NOs: 16 and 19; Arabidopsis protein At5g42810 (GenBank accession # NP_568613; SEQ ID NO:6) and At1g22100 (GenBank accession # NP_173629; SEQ ID NO:7); Rice protein OSJNBa0015K02.18 (GenBank accession # CAE02901; SEQ ID NO:10); Brassica protein (SEQ ID NO:8) assembled from Brassica napus EST BN45.053K04F020108 (GenBank # CD837809), BN40.063H24F01 1229 (GenBank # CD832483), BN40.062L06F01 1227 (GenBank # CD832284) and BN25.068E01F020124 (GenBank # CD827663).

DETAILED DESCRIPTION OF THE INVENTION

Figure 1:
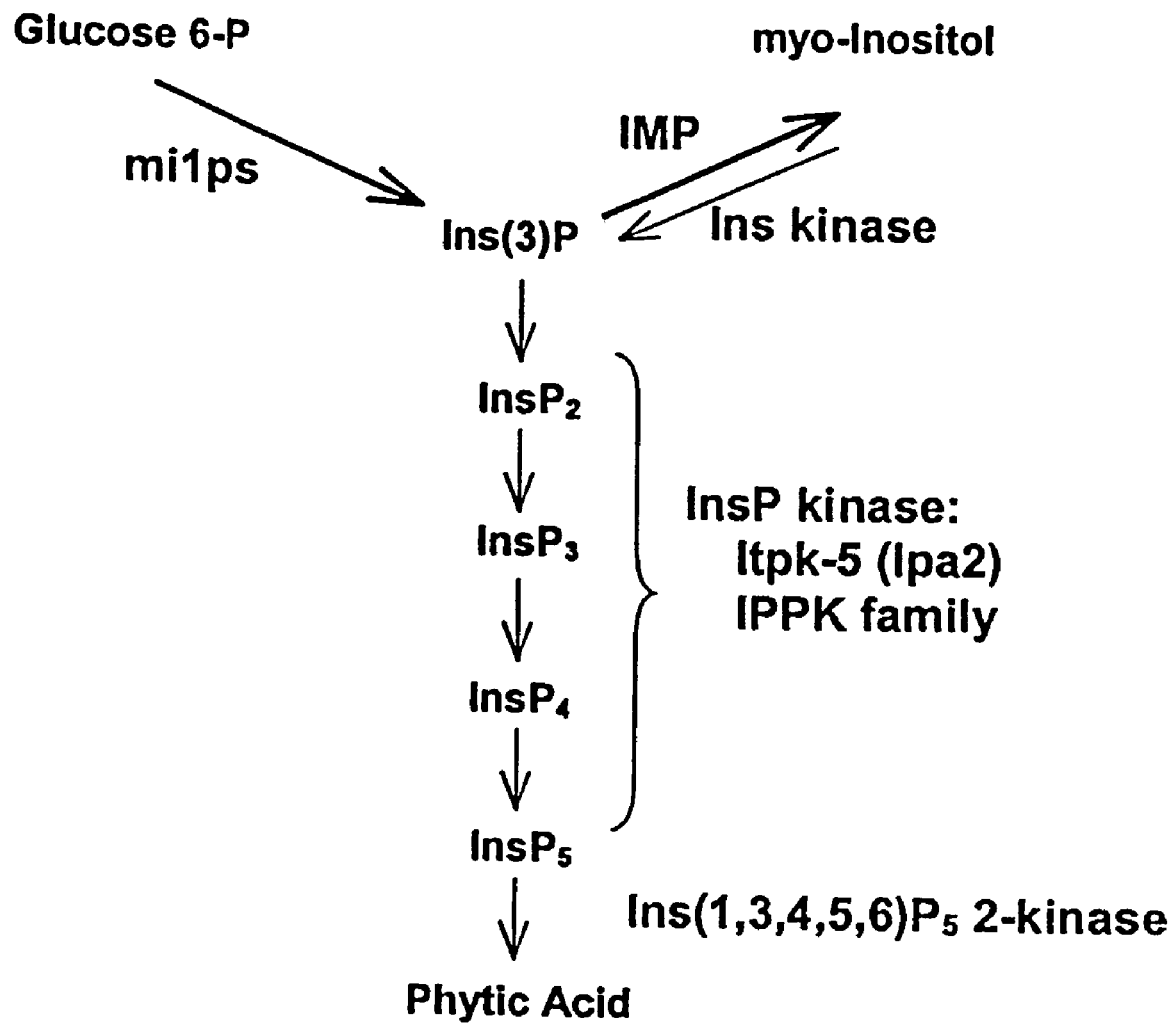
FIG. 1 shows a diagram of the phytic acid pathway in seeds and the genes of interest.
Figure 2:
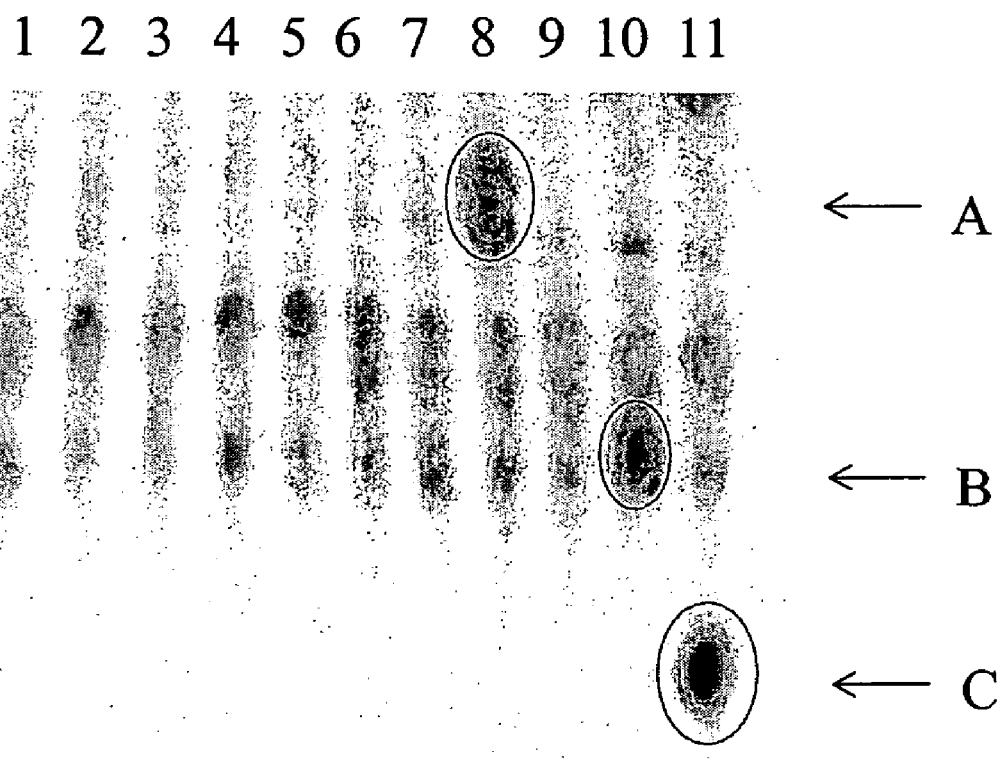
FIG. 2 shows results of an InsP kinase activity assay on IP2K-1 protein; see description in Example 2. Arrow A indicates the location of $InsP_4$; arrow B indicates the location of $InsP_5$; and arrow C indicates the location of phytic acid. InsP substrates tested were: Ins(1,3,4)$P_3$ (shown in lane #1 in figure); Ins(1,4,5)$P_3$ (lane #2); Ins(1,5,6)$P_3$ (lane #3); Ins(2,4,5) $P_3$ (lane #4); Ins(3,5,6)$P_3$ (lane #5); Ins(1,2,5,6)$P_4$ (lane #6); Ins(1,3,4,5)$P_4$ (lane #7); Ins(1,3,4,6)$P_4$ (lane #8); Ins(1,3,5, 6)$P_4$ (lane #9); Ins(3,4,5,6)$P_4$ (lane #10); Ins(1,3,4,5,6)$P_5$ (lane #11)

The invention is drawn to compositions and methods for modulating the level of phytate in plants. More specifically, the isolated nucleic acids of the invention comprise nucleotide sequences that encode IP2Ks of the invention as well as fragments and variants thereof. In particular, the present invention provides for isolated nucleic acid molecules comprising nucleotide sequences as set forth in SEQ ID NO:15 (IP2K-1) or SEQ ID NO:17 (IP2K-2), or encoding the amino acid sequences shown in SEQ ID NO:16 or SEQ ID NO:18. In addition, the invention provides nucleic acids comprising the complements of these nucleotide sequences. The disclosed IP2K proteins have Ins(1,3,4,5,6)$P_5$2-kinase (IP2K) activity and in some embodiments also display kinase activity on Ins(3,4,5,6)$P_4$.

The compositions of the invention comprise isolated nucleic acids that encode IP2K proteins, fragments and variants thereof, cassettes comprising nucleotide sequences of the invention, and isolated IP2K proteins. The compositions also include nucleic acids comprising nucleotide sequences which are the complement, or antisense, of these IP2K nucleotide sequences. The invention further provides plants and microorganisms transformed with these novel nucleic acids as well as methods involving the use of such nucleic acids, proteins, and transformed plants in producing food and feed with reduced phytate and/or increased non-phytate phosphorus levels.

In some embodiments, phytate is reduced or eliminated by transforming a maize plant cell with an expression cassette that expresses a polynucleotide that inhibits the expression of the IP2K enzyme. The polynucleotide may inhibit the expression of one or more IP2Ks directly, by preventing translation of the IP2K messenger RNA, or indirectly, by encoding a polypeptide that inhibits the transcription or translation of a maize gene encoding an IP2K. Methods for inhibiting or eliminating the expression of a gene in a plant are well known in the art, and any such method may be used in the present invention to inhibit the expression of one or more maize IP2Ks.

In accordance with the present invention, the expression of an IP2K protein is inhibited if the protein level of the IP2K is statistically lower than the protein level of the same IP2K in a plant that has not been genetically modified or mutagenized to inhibit the expression of that IP2K. In particular embodiments of the invention, the protein level of the IP2K in a modified plant according to the invention is less than 95%, less than 90%, less than 85%, less than 80%, less than 70%, less than 60%, less than 50%, less than 40%, less than 30%, less than 20%, less than 10%, or less than 5% of the protein level of the same IP2K in a plant that is not a mutant or that has not been genetically modified to inhibit the expression of that IP2K. The expression level of the IP2K may be measured directly, for example, by assaying for the level of IP2K expressed in the maize cell or plant, or indirectly, for example, by measuring the activity of the IP2K enzyme in the maize cell or plant. Methods for determining the activity of IP2Ks are described elsewhere herein. The activity of an IP2K protein is "eliminated" according to the invention when it is not detectable by the assay methods described elsewhere herein.

In other embodiments of the invention, the activity of one or more maize IP2Ks is reduced or eliminated by transforming a plant cell with an expression cassette comprising a polynucleotide encoding a polypeptide that inhibits the activity of one or more IP2Ks. The activity of an IP2K is inhibited according to the present invention if the phytate content of the transformed plant or cell is statistically lower than the phytate content of a plant that has not been genetically modified to inhibit the activity of that IP2K. In particular embodiments of the invention, the phytate content of the modified plant according to the invention is less than 95%, less than 90%, less than 85%, less than 80%, less than 70%, less than 60%, less than 50%, less than 40%, less than 30%, less than 20%, less than 10%, or less than 5% of the phytate content of the same plant that that has not been genetically modified to inhibit the expression of that IP2K.

In other embodiments, the activity of an IP2K may be reduced or eliminated by disrupting the gene encoding the IP2K. The invention encompasses mutagenized plants that carry mutations in IP2K genes, where the mutations reduce expression of the IP2K gene or inhibits the activity of the encoded IP2K.

Thus, many methods may be used to reduce or eliminate the activity of an IP2K. More than one method may be used to reduce the activity of a single plant IP2K. In addition, combinations of methods may be employed to reduce or eliminate the activity of two or more different IP2Ks.

Non-limiting examples of methods of reducing or eliminating the expression of a plant IP2K are given below.

In some embodiments of the present invention, a plant cell is transformed with an expression cassette that is capable of expressing a polynucleotide that inhibits the expression of IP2K. The term "expression" as used herein refers to the biosynthesis of a gene product, including the transcription and/or translation of said gene product. For example, for the purposes of the present invention, an expression cassette capable of expressing a polynucleotide that inhibits the expression of at least one maize IP2K is an expression cassette capable of producing an RNA molecule that inhibits the transcription and/or translation of at least one maize IP2K. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an IP2K are given below.

In some embodiments of the invention, inhibition of the expression of IP2K may be obtained by sense suppression or cosuppression. For cosuppression, an expression cassette is designed to express an RNA molecule corresponding to all or part of a messenger RNA encoding an IP2K in the "sense" orientation. Overexpression of the RNA molecule can result in reduced expression of the native gene. Accordingly, multiple plant lines transformed with the cosuppression expression cassette are screened to identify those that show the greatest inhibition of IP2K expression.

The polynucleotide used for cosuppression may correspond to all or part of the sequence encoding the IP2K, all or part of the 5' and/or 3' untranslated region of an IP2K transcript, or all or part of both the coding sequence and the untranslated regions of a transcript encoding IP2K. In some embodiments where the polynucleotide comprises all or part of the coding region for the IP2K, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin et al. (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference.

In some embodiments of the invention, inhibition of the expression of the IP2K may be obtained by antisense suppression. For antisense suppression, the expression cassette is designed to express an RNA molecule complementary to all or part of a messenger RNA encoding the IP2K. Overexpression of the antisense RNA molecule can result in reduced expression of the native gene. Accordingly, multiple plant lines transformed with the antisense suppression expression cassette are screened to identify those that show the greatest inhibition of IP2K expression.

The polynucleotide for use in antisense suppression may correspond to all or part of the complement of the sequence encoding the IP2K, all or part of the complement of the 5' and/or 3' untranslated region of the IP2K transcript, or all or part of the complement of both the coding sequence and the untranslated regions of a transcript encoding the IP2K. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. patent Publication No. 20020048814, herein incorporated by reference.

In some embodiments of the invention, inhibition of the expression of an IP2K may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of IP2K expression. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

In some embodiments of the invention, inhibition of the expression of one or more IP2Ks may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407: 319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407:319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz et al. (2002) *PNAS* 99 (Suppl. 4): 16499-16506; Mette et al. (2000) *EMBO J.* 19(19):5194-5201).

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for IP2K). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

In some embodiments, the polynucleotide expressed by the expression cassette of the invention is catalytic RNA or has ribozyme activity specific for the messenger RNA of IP2K. Thus, the polynucleotide causes the degradation of the endogenous messenger RNA, resulting in reduced expression of the IP2K. This method is described, for example, in U.S. Pat. No. 4,987,071, herein incorporated by reference.

In some embodiments of the invention, inhibition of the expression of one or more IP2Ks may be obtained by RNA interference by expression of a gene encoding a micro RNA (miRNA). miRNAs are regulatory agents consisting of about 22 ribonucleotides. miRNAs are highly efficient at inhibiting the expression of endogenous genes. See, for example Javier et al. (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of IP2K expression, the 22-nucleotide sequence is selected from an IP2K transcript sequence and contains 22 nucleotides of said IP2K sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In one embodiment, the polynucleotide encodes a zinc finger protein that binds to a gene encoding an IP2K resulting in reduced expression of the gene. In particular embodiments, the zinc finger protein binds to a regulatory region of an IP2K gene. In other embodiments, the zinc finger protein binds to a messenger RNA encoding an IP2K and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. patent Publication No. 20030037355; each of which is herein incorporated by reference.

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima et al. (1998) *Virology* 243:472-481; Okubara et al. (1994) *Genetics* 137:867-874; and Quesada et al. (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See McCallum et al. (2000) *Nat. Biotechnol.* 18:455-457, herein incorporated by reference.

Mutations that impact gene expression or that interfere with the function of the encoded protein are well known in the art. Insertional mutations in gene exons usually result in null-mutants. Mutations in conserved residues are particularly effective in inhibiting the IP2K activity of the encoded protein. Conserved residues of plant IP2Ks suitable for mutagenesis with the goal to eliminate IP2K activity are described herein, as shown for example in FIGS. 3 and 4 and in the conserved domains set forth in SEQ ID NOs: 1-5. Such mutants can be isolated according to well-known procedures, and mutations in different IP2K loci can be stacked by genetic crossing. See, for example, Gruis et al. (2002) *Plant Cell* 14:2863-2882.

In another embodiment of this invention, dominant mutants can be used to trigger RNA silencing due to gene inversion and recombination of a duplicated gene locus. See, for example, Kusaba et al. (2003) *Plant Cell* 15:1455-1467.

The invention encompasses additional methods for reducing or eliminating the activity of one or more IP2Ks. Examples of other methods for altering or mutating a genomic nucleotide sequence in a plant are known in the art and include, but are not limited to, the use of DNA:RNA vectors, DNA:RNA mutational vectors, DNA:RNA repair vectors, mixed-duplex oligonucleotides, self-complementary DNA:RNA oligonucleotides, and recombinogenic oligonucleobases. Such vectors and methods of use are known in the art. See, for example, U.S. Pat. Nos. 5,565,350; 5,731, 181; 5,756,325; 5,760,012; 5,795,972; and 5,871,984; each of which are herein incorporated by reference. See also, WO 98/49350, WO 99/07865, WO 99/25821, and Beetham et al. (1999) *Proc. Natl. Acad. Sci. USA* 96:8774-8778; each of which is herein incorporated by reference.

Where polynucleotides are used to decrease or inhibit IP2K activity, it is recognized that modifications of the exemplary sequences disclosed herein may be made as long as the sequences act to decrease or inhibit expression of the corresponding mRNA. Thus, for example, polynucleotides having at least about 70%, 80%, 85%, 86%, 87%, 88%, 89%, 90%, 91%, 92%, 93%, 94%, 95%, 96%, 97%, 98%, 99%, or 100% sequence identity to the exemplary sequences disclosed herein may be used. Furthermore, portions or fragments of the exemplary sequences or portions or fragments of polynucleotides sharing a particular percent sequence identity to the exemplary sequences may be used to disrupt the expression of the target gene. Generally, sequences of at least 10, 15, 20, 25, 30, 35, 40, 45, 50, 60, 70, 80, 90, 100, 120, 140, 160, 180, 200, 220, 240, 250, 260, 280, 300, 350, 400, 450, 500, 600, 700, 800, 900, 1000, or more nucleotides, or greater may be used. It is recognized that in particular embodiments, the complementary sequence of such sequences may be used. For example, hairpin constructs comprise both a sense and a complementary, or antisense, portion or fragment corresponding to the gene of interest. Antisense constructs may share less than 100% sequence identity with the gene of interest, and may comprise portions or fragments of the gene of interest, so long as the object of the embodiment is achieved, i.e., so long as expression of the gene of interest is decreased.

Accordingly, the methods of the invention include methods for modulating the levels of endogenous transcription and/or gene expression by transforming plants with antisense or sense constructs to produce plants with reduced levels of phytate. Generally, such modifications will alter the amino acid sequence of the proteins encoded by the genomic sequence as to reduce or eliminate the activity of a particular endogenous gene, such as IP2K, in a plant or part thereof, for example, in a seed.

Furthermore, it is recognized that the methods of the invention may employ a nucleotide construct that is capable of directing, in a transformed plant, the expression of at least one protein, or the transcription of at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or transcription of an RNA.

In addition, it is recognized that where the transformation methods involve a nucleotide construct, methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. In some embodiments, an "isolated" nucleic acid is free of sequences (such as protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, culture medium in some embodiments represents less than about 30%, 20%, 10%, 5%, or 1% (by dry weight) of chemical precursors or non-protein-of-interest chemicals.

The article "a" and "an" are used herein to refer to one or more than one (i.e., to at least one) of the grammatical object of the article. By way of example, "an element" means one or more element.

The terms "modulating" or "modulate" as used herein indicate that the level or amount of a product is increased or decreased in accordance with the goal of the particular embodiment. For example, if a particular embodiment were useful for producing purified IP2K enzyme, it would be desirable to increase the amount of IP2K protein produced. The term "expression" generally refers to the translation of a particular mRNA into a protein; however, in some contexts, "expression" refers to the overall process of production of a protein and therefore includes both transcription of an mRNA and translation of the corresponding protein.

Fragments and variants of the disclosed nucleotide sequences and proteins encoded thereby are also encompassed by the present invention. The term "fragment" refers to a portion of the nucleotide sequence or a portion of the amino acid sequence and hence protein encoded thereby, if any. Fragments of a nucleotide sequence may encode protein fragments that retain the biological activity of the native protein and hence have IP2K activity. Alternatively, fragments of a nucleotide sequence that are useful as hybridization probes or in sense or antisense suppression generally do not encode fragment proteins retaining biological activity. Thus, fragments of a nucleotide sequence may range from at least about 20 contiguous nucleotides, about 50 contiguous nucleotides, about 100 contiguous nucleotides, and up to the full-length nucleotide sequence encoding the proteins of the invention.

A fragment of an IP2K nucleotide sequence that encodes a biologically active portion of an IP2K protein of the invention will encode at least 15, 25, 30, 50, 100, 150, 200, 250, 300, 350, or 400 contiguous amino acids, or up to the total number of amino acids present in a full-length IP2K protein of the invention (for example, 440 amino acids for SEQ ID NO:16 or SEQ ID NO: 18). Fragments of an IP2K nucleotide sequence that are useful in non-coding embodiments, for example, as PCR primers or for sense or antisense suppression, generally need not encode a biologically active portion of an IP2K protein.

Thus, a fragment of an IP2K nucleotide sequence may encode a biologically active portion of an IP2K protein, or it may be a fragment that can be used, for example, as a hybridization probe or in sense or antisense suppression using methods disclosed herein and known in the art. A biologically active portion of an IP2K protein can be prepared by isolating a portion of one of the IP2K nucleotide sequences of the invention, expressing the encoded portion of the IP2K protein (e.g., by recombinant expression in vitro), and assessing the activity of the encoded portion of the IP2K protein. Nucleic acid molecules that are fragments of an IP2K nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, or 1,800 nucleotides, or up to the number of nucleotides present in a full-length IP2K nucleotide sequence disclosed herein (for example, 1936 nucleotides for SEQ ID NO:15 and 1856 nucleotides for SEQ ID NO:17).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the IP2K polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an IP2K protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 16 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, IP2K activity as described herein. Such variants may result from, for example, genetic polymorphism or from human manipulation. Biologically active variants of a native IP2K protein of the invention will have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the IP2K proteins can be prepared by the creation of mutations in the DNA. Methods for mutagenesis and nucleotide sequence alterations are well known in the art. See, for example, Kunkel (1985) *Proc. Natl. Acad. Sci. USA* 82: 488-492; Kunkel et aL (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Nat'l. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired IP2K activity. Obviously, the mutations that will be made in the DNA encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by the methods used in Examples 2 and 8 and references cited therein.

Variant nucleotide sequences and proteins also encompass sequences and proteins derived from a mutagenic and recombinogenic procedure such as DNA shuffling. With such a procedure, one or more different IP2K coding sequences can be manipulated to create a new IP2K possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the IP2K gene of the invention and other known IP2K genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91: 10747-10751; Stemmer (1994) *Nature* 370: 389-391; Crameri et al. (1997) *Nature Biotech.* 15: 436-438; Moore et al. (1997) *J. Mol. Biol.* 272: 336-347; Zhang et al. (1997) *Proc. Natl. Acad. Sci. USA* 94: 4504-4509; Crameri et al. (1998) *Nature* 391: 288-291; and U.S. Pat. Nos. 5,605,793 and 5,837,458.

The present invention further provides a method for modulating (i.e., increasing or decreasing) the concentration or composition of the polypeptides of the claimed invention in a plant or part thereof. Modulation can be effected by increasing or decreasing the concentration and/or the composition (i.e., the ratio of the polypeptides of the claimed invention) in a plant.

In some embodiments, the method comprises transforming a plant cell with a cassette comprising a polynucleotide of the invention to obtain a transformed plant cell, growing the transformed plant cell under conditions allowing expression of the polynucleotide in the plant cell in an amount sufficient to modulate concentration and/or composition of the corresponding protein in the plant cell. In some embodiments, the method comprises utilizing the polynucleotides of the invention to create a deletion or inactivation of the native gene. Thus, a deletion may constitute a functional deletion, i.e., the creation of a "null" mutant, or it may constitute removal of part or all of the coding region of the native gene. Methods for creating null mutants are well-known in the art.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein.

In addition to sense and antisense suppression, catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al. (1988) *Nature* 334: 585-591.

A variety of cross-linking agents, alkylating agents and radical-generating species as pendant groups on polynucleotides of the present invention can be used to bind, label, detect, and/or cleave nucleic acids. For example, Vlassov et al. (1986) *Nucl. Acids Res.* 14: 4065-4076 describes covalent bonding of a single-stranded DNA fragment with alkylating derivatives of nucleotides complementary to target sequences. Similar work is reported in Knorre et al. (1985) *Biochimie* 67: 785-789. Others have also showed sequence-specific cleavage of single-stranded DNA mediated by incorporation of a modified nucleotide which was capable of activating cleavage (Iverson and Dervan (1987) *J. Am. Chem. Soc.* 109: 1241-1243). Meyer et al. ((1989) *J. Am. Chem. Soc.* 111: 8517-8519) demonstrated covalent crosslinking to a target nucleotide using an alkylating agent complementary to the single-stranded target nucleotide sequence. Lee et al. ((1988) *Biochemistry* 27: 3197-3203) disclosed a photoactivated crosslinking to single-stranded oligonucleotides mediated by psoralen. Home et al. ((1990) *J. Am Chem. Soc.* 112: 2435-2437) used crosslinking with triple-helix-forming probes. Webb and Matteucci ((1986) *J. Am. Chem. Soc.* 108: 2764-2765) and Feteritz et al. ((1991) *J. Am. Chem. Soc.* 113: 4000) used N4, N4-ethanocytosine as an alkylating agent to crosslink to single-stranded oligonucleotides. In addition, various compounds to bind, detect, label, and/or cleave nucleic acids are known in the art. See, for example, U.S. Pat. Nos. 5,543,507; 5,672,593; 5,484,908; 5,256,648; and 5,681, 941. Such embodiments are collectively referred to herein as "chemical destruction."

In some embodiments, an isolated nucleic acid (e.g., a vector) comprising a promoter sequence is transfected into a plant cell. Subsequently, a plant cell comprising the promoter operably linked to a nucleic acid comprising a nucleotide sequence of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant-forming conditions for a time sufficient to modulate the concentration and/or composition of polypeptides of the present invention in the plant. Plant forming conditions are well known in the art.

In general, when an endogenous polypeptide is modulated using the methods of the invention, the content of the polypeptide in a plant or part or cell thereof is increased or decreased by at least 5%, 10%, 20%, 30%, 40%, 50%, 60%, 70%, 80%, 90%, or more relative to a native control plant, plant part, or cell lacking the aforementioned cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire IP2K sequences set forth herein or to fragments thereof are encompassed by the present invention. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode an IP2K protein and which hybridize under stringent conditions to the IP2K sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the IP2K sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire IP2K sequences disclosed herein, or one or more portions thereof, may be used as probes capable of specifically hybridizing to corresponding IP2K sequences and messenger RNAs. To achieve specific hybridization under a variety of conditions, such probes can include sequences that are unique among IP2K sequences and are at least about 10, 12, 15, 16, 17, 18, 19, or 20 nucleotides in length. Such probes may be used to amplify corresponding IP2K sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. The terms "stringent conditions" or "stringent hybridization conditions" refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% fonnamide, 1.0 M NaCl, 1% SDS at 37° C., and a wash in 0.5X to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, "% form" is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. The duration of the wash time will be at least a length of time sufficient to reach equilibrium, or at least 30 minutes, one hour, or two hours. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, or 100 nucleotides in length, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local-alignment-method of Pearson and Lipman (1988) *Proc. Natl. Acad. Sci.* 85: 2444-2448; the algorithm of Karlin and Altschul (1990) *Proc. Natl. Acad. Sci. USA* 87: 2264, modified as in Karlin and Altschul (1993) *Proc. Natl. Acad. Sci. USA* 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73: 237-244 (1988); Higgins et al. (1989) *CABIOS* 5: 151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215: 403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2; and the BLOSUM62 scoring matrix or any equivalent program thereof. The term "equivalent program" refers to any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 90%, or 95% sequence identity to a reference sequence when compared using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, or 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, or 95% sequence identity to the reference sequence over a specified comparison window. In some embodiments, optimal alignment is conducted using the homology alignment algorithm of Needleman and Wunsch (1970) *J. Mol. Biol.* 48: 443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The IP2K sequences of the invention are provided in cassettes for transcription and/or expression in the plant of interest. The cassette will include 5' and 3' regulatory sequences operably linked to an IP2K sequence of the invention. The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple cassettes.

Such a cassette is provided with a plurality of restriction sites for insertion of the IP2K sequence to be under the transcriptional regulation of the regulatory regions. The cassette may additionally contain selectable marker genes. If protein expression is desired, the cassette may be referred to as an expression cassette and will include in the 5'-3' direction of transcription: a transcriptional and translational initiation region (i.e., a promoter), an IP2K nucleotide sequence of the invention, and a transcriptional and translational termination region (i.e., termination region) functional in plants. In any cassette, the promoter may be native or analogous, or foreign or heterologous, to the plant host and/or to the nucleotide sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the nucleotide sequence of the invention, it is intended that the promoter is not the native or naturally-occurring promoter for the operably-linked nucleotide sequence of the invention.

While it may be preferable to transcribe or express sequences using heterologous promoters, native promoter sequences may also be used. Such constructs change transcription and/or expression levels of IP2K in the plant or plant cell. Thus, the phenotype of the plant or plant cell is altered.

In a cassette, the termination region may be native with the transcriptional initiation region, may be native with the operably linked nucleotide sequence of interest, may be native with the plant host, or may be derived from another source (i.e., foreign or heterologous to the promoter, the nucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262: 141-144; Proudfoot (1991) *Cell* 64: 671-674; Sanfacon et al. (1991) *Genes Dev.* 5: 141-149; Mogen et al. (1990) *Plant Cell* 2: 1261-1272; Munroe et al. (1990) *Gene* 91: 151-158; Ballas et al. (1989) *Nucleic Acids Res.* 17: 7891-7903; and Joshi et al. (1987) *Nucleic Acid Res.* 15: 9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17: 477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell, and the sequence may be modified to avoid predicted hairpin secondary mRNA structures.

The cassettes may additionally contain 5' leader sequences in the cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus) and human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

Generally, the cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate amnmonium, bromoxynil, imidazolinones, and 2,4-dichlorophenoxyacetate (2,4-D). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Aci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); Gill et al. (1988) *Nature* 334: 721-724. Such disclosures are herein incorporated by reference.

The above list of selectable marker genes is not meant to be limiting. Any suitable selectable marker gene can be used in the present invention, and one of skill in the art will be able to determine which selectable marker gene is suitable for a particular application.

In preparing the cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3: 2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the transcription and/or expression of a particular nucleotide sequence in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88: 10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227: 229-237, and U.S. Pat. Nos. 5,814,618 and 5,789,156), herein incorporated by reference.

Tissue-preferred promoters can be utilized to target enhanced IP2K transcription and/or expression within a particular plant tissue. Tissue-preferred promoters include those described in Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505. Such promoters can be modified, if necessary, for weak expression.

Leaf-specific promoters are known in the art. See, for example, Yamamoto et al. (1997) *Plant J.* 12(2): 255-265; Kwon et al. (1994) *Plant Physiol.* 105: 357-67; Yamamoto et al. (1994) *Plant Cell Physiol.* 35(5): 773-778; Gotor et al. (1993) *Plant J.* 3: 509-18; Orozco et al. (1 993) *Plant Mol. Biol.* 23(6): 1129-113 8; and Matsuoka et al. (1993) *Proc. Natl. Acad. Sci. USA* 90(20): 9586-9590.

Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3): 433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1): 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4): 759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177 and U.S. Pat. No. 6,225,529, herein incorporated by reference). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Where low level transcription or expression is desired, weak promoters will be used. Generally, the term "weak promoter" refers to a promoter that drives transcription and/or expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of transcription and/or expression. Where a promoter is expressed at unacceptably high levels, portions of the promoter sequence can be deleted or modified to decrease transcription and/or expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) *Science* 233: 478-481.

Chloroplast targeting sequences are known in the art and include the chloroplast small subunit of ribulose-1,5-bisphosphate carboxylase (Rubisco) (de Castro Silva Filho et al.

(1996) *Plant Mol. Biol.* 30:769-780; Schnell et al. (1991) *J. Biol. Chem.* 266(5): 3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11): 6081-6087); plastocyanin (Lawrence et al. (1997) *J. Biol. Chem.* 272(33): 20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263: 14996-14999). See also Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) *Science* 233: 478-481.

Methods for transformation of chloroplasts are known in the art. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91: 7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In specific embodiments, the IP2K sequences of the invention can be provided to a plant using a variety of transient transformation methods. Such transient transformation methods include, but are not limited to, the introduction of the IP2K protein or variants and fragments thereof directly into the plant or the introduction of an IP2K transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the IP2K polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In certain embodiments the nucleic acid sequences of the present invention can be "stacked" with any combination of nucleic acids of interest in order to create plants with a desired phenotype. The terms "stacked" or "stacking" indicate that a plant of interest is transformed with one or more nucleic acids comprising multiple nucleotide sequences so that the transcription and/or expression of multiple endogenous genes are altered in the plant. For example, antisense nucleic acids of the present invention may be stacked with other nucleic acids which comprise a sense or antisense nucleotide sequence of IPTK-5 (e.g., SEQ ID NO: 14) and/or inositol polyphosphate kinase (IPPK, e.g., SEQ ID NO: 13), or with sense or antisense nucleic acids of other genes implicated in phytic acid metabolic pathways such as phytase, Lpa1 (also called MRP; see SEQ ID NO: 20), Lpa2 (see U.S. Pat. Nos. 5,689,054 and 6,111,168); myo-inositol 1-phosphate synthase (MIIPS), myo-inositol kinase (also known as MIK, CHOK, or Lpa3; see SEQ ID NO: 21), and myo-inositol monophosphatase (IMP) (see WO 99/05298 and U.S. application Ser. No. 10/042,465, filed Jan. 9, 2002), the disclosures of which are herein incorporated by reference, and the like. The addition of such nucleic acids could enhance the reduction of phytic acid and InsP intermediates, thereby providing a plant with more bioavailable phosphate and/or reduced phytate. The nucleic acids of the present invention can also be stacked with any other gene or combination of genes to produce plants with a variety of desired trait combinations.

These stacked combinations can be created by any method including but not limited to cross breeding plants by any conventional or TopCross methodology, or genetic transformation. If the traits are stacked by genetically transforming the plants, the nucleic acids of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of cassettes suitable for transformation. For example, if two sequences will be introduced, the two sequences can be contained in separate cassettes (trans) or contained on the same transformation cassette (cis). Transcription and/or expression of the sequences can be driven by the same promoter or by different promoters. In certain cases, it may be desirable to introduce a cassette that will suppress the expression of the polynucleotide of interest. This may be combined with any combination of other cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

It is understood that in some embodiments the nucleic acids to be stacked with IP2K can also be designed to reduce or eliminate the expression of a particular protein, as described in detail herein for IP2K. Thus, the methods described herein with regard to the reduction or elimination of expression of IP2K are equally applicable to other nucleic acids and nucleotide sequences of interest, such as, for example, IPPK, ITPK-5, myo-inositol kinase (MIK), and MRP (Lpa1). Accordingly, the descriptions herein of IP2K fragments, variants, and other nucleic acids and nucleotide sequences apply equally to other nucleic acids and nucleotide sequences of interest such as IPPK, ITPK-5, myo-inositol kinase (MIK), and MRP (Lpa1). For example, an antisense construct could be designed for IPPK comprising a nucleotide sequence that shared 90% sequence identity to SEQ ID NO:13 or was a 50-nucleotide fragment of the complement of SEQ ID NO:13, as more particularly described herein for IP2K.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Transformation protocols as well as protocols for introducing nucleotide sequences into plants may vary depending on the type of plant or plant cell, i.e., monocot or dicot, targeted for transformation. Suitable methods of introducing nucleic acids into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3: 2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6: 923-926); and Lec1 transformation (WO 00/28058). Also see Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87:671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6: 559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having the desired phenotypic characteristic identified. Two or more generations may be grown to ensure that the desired phenotypic characteristic is stably maintained and inherited and then seeds harvested to ensure that stable transformants exhibiting the desired phenotypic characteristic have been achieved. In this manner, the present invention provides transformed seed (also referred to as "transgenic seed") having a nucleotide construct of the invention, for example, a cassette of the invention, stably incorporated into their genome.

The present invention may be used for transformation of any plant species, including, but not limited to, monocots and dicots. Examples of plant species of interest include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*). In some embodiments, plants of the present invention are crop plants (for example, corn, alfalfa, sunflower, Brassica, soybean, cotton, safflower, peanut, sorghum, wheat, millet, tobacco, etc.).

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The methods of the invention involve introducing a nucleotide construct into a plant. The term "introducing" refers to presenting to the plant the nucleotide construct (i.e., DNA or RNA) or a polypeptide in such a manner that the nucleotide construct or the polypeptide gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

The term "stable transformation" indicates that the nucleotide construct introduced into a plant integrates into the genome of the plant and is capable of being inherited by progeny thereof. Such plants are referred to as "stably transformed" or "stable transformants." The term "transient transformation" indicates that a nucleotide construct introduced into a plant does not integrate into the genome of the plant. Thus, "transformation" refers to either stable or transient transformation, and "transformant" refers to plants which have been either stably or transiently transformed.

Thus, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention may be introduced into plants by contacting plants with a virus or viral nucleic acids. Generally, such methods involve incorporating a nucleotide construct of the invention within a viral DNA or RNA molecule. It is recognized that an IP2K of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191; 5,889,190; 5,866,785; 5,589,367; and 5,316,931, herein incorporated by reference.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

EXPERIMENTAL

EXAMPLE 1

Expression and Purification of Zm-IP2K

Fungal and human Ins(1,3,4,5,6)$P_5$ 2-kinase ("IP2K") gene sequences were used to identify the maize homologs in a proprietary EST database. The full-length cDNA for both of the maize homologs was then identified and cloned. These cDNAs were cloned into expression vectors and were expressed in E. coli. The proteins were expressed as GST fusion proteins and purified. The purified IP2K proteins showed IP2K activity and also exhibited a novel activity for IP2K proteins. Specifically, the purified IP2K proteins exhibited kinase activity on Ins(3,4,5,6)$P_4$, an activity that was not previously reported.

Protein Sequence Analysis

Figure 3A:
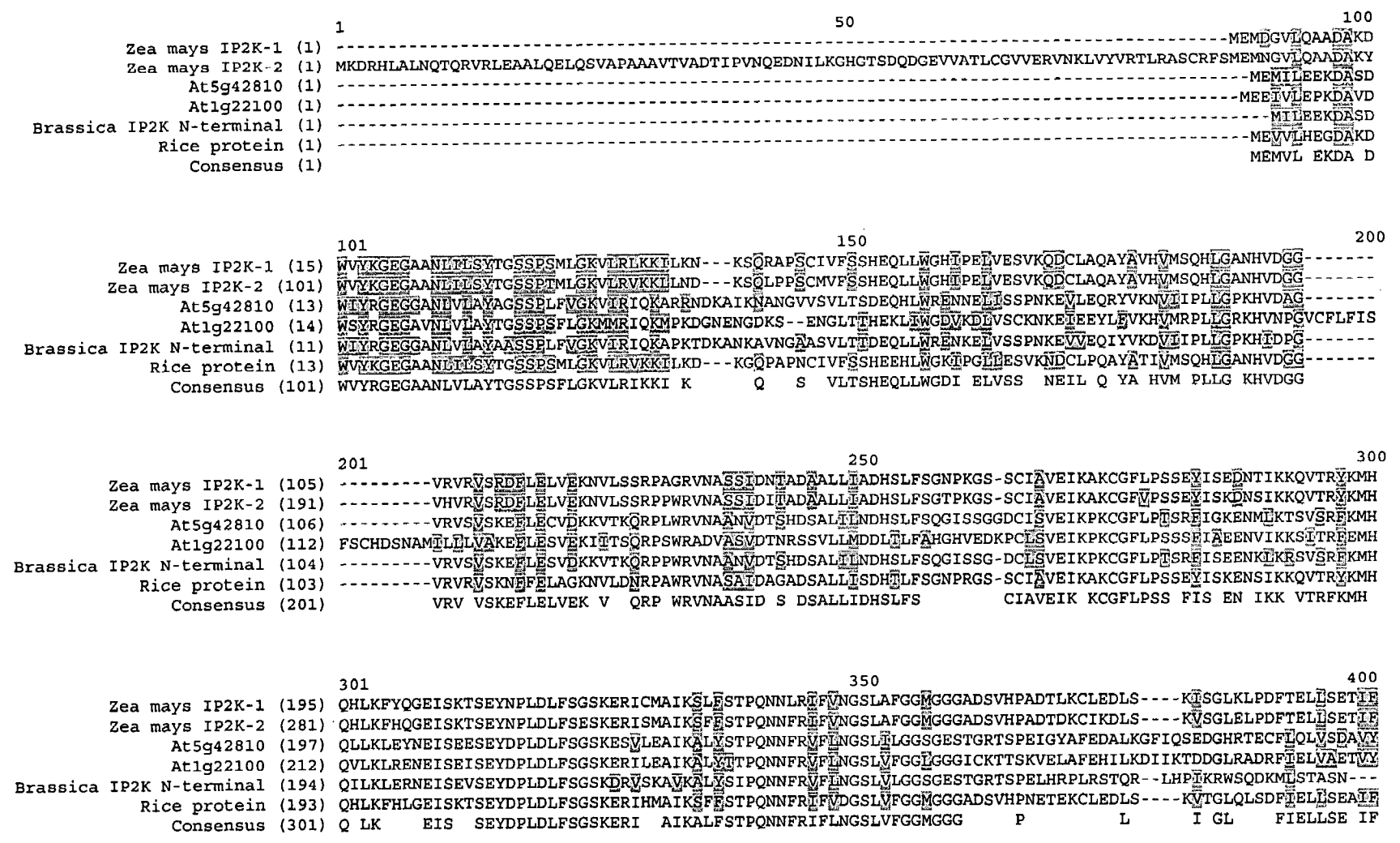

The predicted amino acid sequence of the maize IP2K protein was aligned with other plant proteins. This alignment is shown in FIG. 3. The sequences aligned were as follows: two novel maize IP2K proteins set forth in SEQ ID NOs: 16 and 18; Arabidopsis protein At5g42810 (GenBank accession # NP_568613; SEQ ID NO:6) and At1g22100 (GenBank accession # NP_173629; SEQ ID NO:7); Rice protein OSJNBa0015K02.18 (GenBank accession # CAE02901; SEQ ID NO:10); Brassica protein (SEQ ID NO:8) assembled from Brassica napus EST BN45.053K04F020108 (GenBank # CD837809), BN40.063H24F01 1229 (GenBank # CD832483), BN40.062L06F01 1227 (GenBank # CD832284) and BN25.068E01F020124 (GenBank # CD827663).

Figure 4:
FIG. 4 shows a diagram of the conserved regions that are shared between IP2K and other proteins. The consensus sequences for these regions are set forth in the sequence listing: Domain A, SEQ ID NO:1; Domain B, SEQ ID NO:2; Domain C, SEQ ID NO:3; Domain D, SEQ ID NO:4; Domain E, SEQ ID NO:5.

Five conserved domains were discovered, as shown in FIG. 4. The consensus sequences for these domains are as follows:

```
Domain A (set forth in SEQ ID NO:1)
DAXDW[V,I]Y[K,R]GEG[A,G]ANL[V,I]L[A,S]Y[T,A]GSSPX

[M,F][L,I,V]GK[V,M][L,I,M]R[V,I,L][K,Q]K

Domain B (set forth in SEQ ID NO:2)
C[I,L][A,S]VEIK[A,P]KCGF[L,V]P[S,T]SX[Y,F]IS[K,E]

[E,D]NX[I,L]KK[Q,S][V,I][S,T]R[Y,F]KMHQXLK[F,L]XX

[G,N]EIS[K,E]XSEY[D,N]PLDLFSGSKER[I,V]XXA[I,V]K

[A,S][L,F][F,Y][S,T]TPQNNFR[I,V]F[V,L]NGSL[V,I,A]

[F,L]G

Domain C (set forth in SEQ ID NO:3)
SGVL[G,D]XLLXXQKLDXXDIEGAIHXYYXXIXQPC

Domain D (set forth in SEQ ID NO:4)
[L,M]HS[L,I]P[L,M]D[K,E]SXKI[V,L][K,R]X[F,Y]LI

[S,A]ATAKDCS[I,L,V]MISF
```

-continued

```
Domain E (set forth in SEQ ID NO:5)
[F,Y][D,E]YKX[Y,H]F[I,L,V]DLD[V,L,M]KPL[D,K]KMXXY

[F,Y]KLD[Q,K][K,R]I[V,I,M]NXY
```

Expression and Purification of Zm-IP2K

A single colony of E. coli strain DH5α containing a GST-tagged Zm-IP2K cloned into an expression vector was cultured overnight at 37° C. in LB medium containing ampicillin (Amp). The overnight culture was diluted 1:10 with fresh LB+Amp medium and incubated at 37° C. with vigorous agitation until the A$_{roo}$ reading of the culture was in the range of 0.6 to 2 O.D. units. GST fusion protein expression was induced by the addition of JPTG to the culture to a final concentration of 50 μM. The cultures were incubated at 37° C. with agitation for an additional 3 hours.

Cells were harvested by centrifugation at 7,700×g for 10 minutes at 4° C. Cell pellets were resuspended in ice-cold bacterial lysis buffer (50 mM Tris-HCl, pH 7.4, 100 mM NaCl, 100 μM phenylmethylsulfonyl fluoride). The cells were lysed on ice by sonication. The lysate was clarified by centrifugation at 12,000×g for 10 minutes at 4° C. The GST-ZmIP2K proteins are affinity purified by batch absorption to Glutathione Sepharose 4B slurry per 100 ml clarified lysate. The mixture was incubated for 45 minutes at 4° C. with gentle shaking. As detailed in the manufacturer's instructions, the beads were washed four times with lysis buffer, then two times in phosphate buffered saline. GST-tagged ZmIP2K protein was eluted with 10 mM reduced glutathione in 50 mM Tris-HCl (pH 8.0), 100 mM NaCl. For every 500 ml of cell culture, 200 μl buffer was used to elute the protein. After elution, glycerol was added to a final concentration of 50% and purified GST-ZmIP2K proteins are stored in 50% glycerol at −20° C.

EXAMPLE 2

Assay for Zm-IP2K Activity and Substrate Specificity

Inositol phosphate kinase activities were assayed according to Wilson and Majerus (1996) J. Biol. Chem. 271: 11904-11910 with some modifications. The activity assay was performed in a volume of 25 μl. The assay mixture contained 20 mM HEPES, pH 7.2, 6mM MgCl$_2$, 10 mM LiCl, 1 mM DTT, 40 μM Ins (1,3,4,5,6) P5, 40 μM ATP, 0.5 μl γ-$^{32}$P-ATP (3000 Ci/mmol) and 5 μl enzyme per reaction. The reaction mixture was incubated at 30° C. for 30 minutes. The reaction was stopped by the addition of 2.8 μl stopping solution (3M HCl, 2M KH$_2$PO$_4$) to the 25 μl reaction. One microliter samples of each reaction, along with phytic acid standard, were separated on a polyethyleneimine (PEI)-cellulose thin layer chromatography plate (Merck) with 0.75M HCl according to Spencer et al. ((1990) in Methods in Inositide Research, ed. R.F. Irvine, Raven Press, NY, pp. 29-43). After separation, the TLC plate is air-dried at 70° C., wrapped in plastic wrap and exposed to X-ray film to detect the $^{32}$P-labelled reaction products. The identity of the reaction product is confirmed by comparing the distance migrated to the migration of phytic acid control run on the same TLC plate. In addition to the Ins (1,3,4,5,6)P$_5$, other myo-inositol phosphate substrates also are tested to determine the substrate specificity of the Zm-IP2K1 enzyme. The other substrates tested under the same conditions above included: Ins(1,3,4)P$_3$, Ins(1,4,5)P$_3$, Ins(1,5,6)P$_3$, Ins(2,4,5)P$_3$, Ins(3,5,6)P$_3$, Ins(1,2,5,6)P$_4$, Ins(1,3,4,5)P$_4$, Ins(1,3,4,6)P$_4$, Ins(1,3,5,6)P$_4$, and Ins(3,4,5,6)P$_4$.

Assay results indicated that both Zm-IP2K-1 and Zm-IP2K-2 are capable of phosphorylating the Ins(1,3,4,5,6) P$_5$ substrate to produce $^{32}$P-labelled product that comigrates with phytic acid on PEI-cellulose TLC plates, confirming the expected activity of the enzymes. Further, the Zm-IP2K-1 also used Ins(3,4,5,6)P$_4$ and Ins(1,3,4,6)P$_4$ as a substrate in the in vitro assay. When Ins(3,4,5,6)P$_4$ was used as a substrate, only one InsP$_5$ product was detected, which was probably Ins(2,3,4,5,6)P$_5$. Another possible product from the reaction could be Ins(1,3,4,5,6)P$_5$, but this product should be further phosphorylated to generate phytic acid because of the Ins(1,3,4,5,6)P$_5$ 2-kinase activity of Zm-IP2K-1. In a prolonged incubation with Zm-IP2K1 enzyme, phytic acid is not formed from Ins(3,4,5,6)P$_4$. Therefore, Ins(1,3,4,5,6)P$_5$ can be excluded as a product from Ins(3,4,5,6)P$_4$ phosphorylation by Zm-IP2K1 enzyme.

The Zm-IP2K-1 kinase activity on Ins(3,4,5,6)P$_4$ is a 2-kinase activity, which has not been previously reported. Zm-IP2K-1 also showed kinase activity on Ins(1,3,4,6)P$_4$ and its product is an InsP$_4$, instead of InsP$_5$ as expected. It is possible that the ZmIP2K-1 may also have a phosphatase activity. De-phosphorylation and phosphorylation could result in an InsP$_4$ product when Ins(1,3,4,6)P$_4$ is used as a substrate. Human Ins(1,3,4)P$_3$ 5/6 kinase has been reported to have both InsP phosphatase and kinase activity (Ho et al. (2002) Curr. Biol. 12: 477-482). No kinase activity was detected when any of Ins(1,3,4)P$_3$, Ins(1,4,5)P$_3$, Ins(1,5,6)P$_3$, Ins(2,4,5)P$_3$, Ins(3,5,6)P$_3$, Ins(1,2,5,6)P$_4$, Ins(1,3,4,5)P$_4$ and Ins(1,3,5,6)P$_4$ were used as substrates in the reaction mixture.

EXAMPLE 3

Transformation and Regeneration of Transgenic Plants

Immature maize embryos from greenhouse donor plants are bombarded with a plasmid containing the IP2K nucleotide sequence operably linked to a Glb1 embryo-specific promoter and the selectable marker gene PAT (Wohlleben et al. (1988) Gene 70: 25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the IP2K nucleotide sequence operably linked to a Glb1 promoter is made. This plasmid DNA plus plasmid DNA containing a PAT selectable marker is precipitated onto 1.1 μm (average diameter) tungsten pellets using a CaCl$_2$ precipitation procedure as follows:

100 μl prepared tungsten particles in water
    10 μl (1 μg) DNA in Tris EDTA buffer (1 μg total DNA)
    100 μl 2.5 M CaCl$_2$
    10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are assayed and scored for IP2K activity.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with dI $H_2O$ following adjustment to pH 5.8 with KOH); 2.0 g/l Gelrite™ (added after bringing to volume with dI $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with dI $H_2O$ following adjustment to pH 5.8 with KOH); 3.0 g/l Gelrite™ (added after bringing to volume with dI $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished dI $H_2O$) (Murashige and Skoog (1962) *Physiol. Plant.* 15: 473), 100 mg/l myo-inositol, 0.5 mg/l zeatin, 60 g/l sucrose, and 1.0 ml/l of 0.1 mM abscisic acid (brought to volume with polished dI $H_2O$ after adjusting to pH 5.6); 3.0 g/l Gelrite™ (added after bringing to volume with dI $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished dI $H_2O$), 0.1 g/l myo-inositol, and 40.0 g/l sucrose (brought to volume with polished dI $H_2O$ after adjusting pH to 5.6); and 6 g/l bacto-agar (added after bringing to volume with polished dI $H_2O$), sterilized and cooled to 60° C.

EXAMPLE 4

Production of Transgenic Maize Expressing IP2K

For *Agrobacterium*-mediated transformation of maize with an IP2K nucleotide sequence of the invention, the method of Zhao was employed (U.S. Pat. No. 5,981,840, and PCT patent publication WO98/32326, the contents of which are hereby incorporated by reference). Briefly, immature embryos were isolated from maize and the embryos contacted with a suspension of *Agrobacterium*, where the bacteria are capable of transferring the IP2K nucleotide sequence to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step) on solid medium. Following this co-cultivation period an optional "resting" step was performed in which the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step) after being cultured on solid medium.

EXAMPLE 5

Production of Transgenic Soybean Expressing IP2K

Soybean embryos are bombarded with a plasmid containing the IP2K nucleotide sequence operably linked to a CaMV 35S promoter as follows. To induce somatic embryos, cotyledons 3-5 mm in length are dissected from surface-sterilized, immature seeds of the soybean cultivar A2872 and cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327: 70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313: 810-812), the hygromycin phosphotransferase gene from plasmid pJR225 (from *E. coli*; Gritz et al. (1983) *Gene* 25: 179-188), and the 3' region of the nopaline synthase gene from the T-DNA of the Ti plasmid of *Agrobacterium tumefaciens*. The cassette comprising the IP2K nucleotide sequence operably linked to the CaMV 35S promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm Petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 6

Production of Transgenic Sunflower Plants Expressing IP2K

Sunflower meristem tissues are transformed with an expression cassette containing the IP2K nucleotide sequence operably linked to a CaMV 35S promoter as follows (see also European Patent Number IP 0 486233, herein incorporated by reference, and Malone-Schoneberg et al. (1994) *Plant Science* 103: 199-207). Mature sunflower seed (*Helianthus annuus* L.) are dehulled using a single wheat-head thresher. Seeds are surface sterilized for 30 minutes in a 20% Clorox bleach solution with the addition of two drops of Tween™ 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9: 55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.* 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney et al. (1992) *Plant Mol. Biol.* 18: 301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm Nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the IP2K gene operably linked to the CaMV 35S promoter is introduced into *Agrobacterium* strain EHA 05 via freeze-thawing as described by Holsters et al. (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD600 of about 0.4 to 0.8. The *Agrobacterium* cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an *Agrobacterium* suspension, mixed, and left undisturbed for 30 minutes. The explants are then transferred to GBA medium and cocultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for IP2K activity, for example, as described in Example 2 and/or Example 7.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite™, pH 5.6) and grown under conditions described for explant culture. The upper portion of the seedling is removed, a 1 cm vertical slice is made in the hypocotyl, and the transformed shoot inserted into the cut. The entire area is wrapped with Parafilm™ to secure the shoot. Grafted plants can be transferred to soil following one week of in vitro culture. Grafts in soil are maintained under high humidity conditions followed by a slow acclimatization to the greenhouse environment. Transformed sectors of T$_0$ plants (parental generation) maturing in the greenhouse are identified by NPTII ELISA and/or by IP2K activity analysis of leaf extracts while transgenic seeds harvested from NPTII-positive $T_0$ plants are identified by IP2K activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween™ 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under. 16-hour day and 26° C. incubation conditions.

Explants (around 2 cm long) from two weeks of culture in 374C medium are screened for IP2K activity using assays known in the art or as set forth in Example 2 and/or Example 7. After IP2K-positive explants are identified, those shoots that fail to exhibit IP2K activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for IP2K expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween™ 20 per 100 ml of solution, and are rinsed three times with distilled water. The sterilized seeds are germinated on the filter moistened with water for three days and are then transferred into 48 medium (half-strength MS salt, 0.5% sucrose, 0.3% Gelrite™ pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with Parafilm™. After one week of culture on the medium, grafted plants are transferred to soil. In the first two weeks, they are maintained under high humidity conditions to acclimatize to a greenhouse environment.

EXAMPLE 7

Determination of Phytic Acid, Inositol Phosphates, and Inorganic Phosphate in Transgenic Corn Lines The resulting transformants are screened for inorganic phosphorus and/or phytate levels using the colorimetric assays as described below. The extraction procedure used is compatible with both assays. The calorimetric assays can be performed sequentially or simultaneously. Putative events are usually initially screened for increased levels of inorganic phosphorous compared to wild type control and then further characterized by the phytate assay.

A. $P_i$ Assay

A rapid test was used to assay inorganic phosphate content in kernels. Individual kernels were placed in a 25-well plastic tray and crushed at 2000 psi using a hydraulic press. Two milliliters of 1N $H_2SO_4$ were added into each sample and incubated at room temperature for 2 hours. Four milliliters of 0.42% ammonium molybdate-1N $H_2SO_4$:10% ascorbic acid (6:1) was added. In the case of an increased inorganic phosphate content, blue color developed in 20 minutes. Non-mutant kernels served as a negative control and mutant lpa2 kernels as a positive control.

B. Determination of Phytic Acid and Inorganic Phosphate

Phytic acid and inorganic phosphate in dry, mature seeds were assayed according to modifications of the methods described by Haug and Lantzsch (1983) *J. Sci. Food Agric.* 34: 1423-1426 and Chen et al. ((1956) *Anal. Chem.* 28: 1756-1758), respectively. Single kernels were ground using a Geno/Grinder2000 (Sepx CertiPrep, Metuchen, N.J.). Twenty-five to thirty-five milligram samples were placed into 1.5-ml Eppendorf tubes. One milliliter of 0.4 N HCl was added, and the tubes were shaken on a gyratory shaker at room temperature for 3.5 hours. The tubes were then centrifuged at 3,900 g for 15 min. Supernatants were transferred into fresh tubes and used for both phytic acid and inorganic phosphate determinations. Measurements were performed in duplicate.

For the phytic acid assay, 35 µl of each extract was placed into wells of a 96-well microtiter plate. Thirty-five microliters of distilled $H_2O$ and 140 µl of 0.02% ammonium iron (III) sulphate-0.2 N HCl were added to each sample. The plate was covered with a rubber lid and heated in a thermal cycler at 99° C. for 30 min. The plate was cooled to 4° C., kept on an ice-water bath for 15 min, and then left at room temperature for 20 minutes. The plate was sealed with sticky foil and centrifuged at 3,900 g at 24° C. for 30 minutes. Eighty microliters of each supernatant were placed into wells of a fresh 96-well-plate, 120 µl of 1% 2,2'-bipyridine-1% thioglycolic acid was added to each well, and then absorbance was recorded at 519 nm using a VERSAmax™ microplate reader (Molecular Devices, Sunnyvale, Calif.). Phytic acid content is presented as phytic acid phosphorus (PAP). Authentic phytic acid (Sigma, Cat. No. P-7660) served as a standard. The phytic acid assay may also measure $InsP_5$ and $InSP_4$ if they are present in samples.

To determine inorganic phosphate, 200 µl of each extract was placed into wells of a 96-well microtiter plate. One hundred microliters of 30% aqueous trichloroacetic acid was added to each sample, and the plates were shaken and centrifuged at 3,900 g for 10 min. Fifty microliters of each supernatant were transferred into a fresh plate and 100 µl of 0.42% ammonium molybdate-1N $H_2SO_4$:10% ascorbic acid (7:1) was added. The plates were incubated at 37° C. for 30 min and then absorbance at 800 nm was measured. Potassium phosphate was used as a standard. Inorganic phosphate content is presented as inorganic phosphate phosphorus.

C. Determination of Seed Inositol Phosphates

The presence of significant amounts of inositol phosphates in mature seeds was determined by HPLC according to the Dionex Application Note AN65: Analysis of Inositol Phosphates (Dionex Corporation, Sunnyvale, Calif.). Tissue was ground and mixed as above. Five hundred milligram samples were placed into 20-ml scintillation vials to which 5 ml of 0.4 M HCl was added. The samples were shaken on a gyratory shaker at room temperature for 2 hours and then allowed to sit at 4° C. overnight. Extracts were centrifuged at 1,000 g for 10 min and filtered through a 0.45 µm nylon syringe filter attached to a 5-ml syringe barrel. Just prior to HPLC analysis, 600-µl aliquots were clarified by passing through a 0.22 µm centrifugal filter.

A Dionex DX 500 HPLC with a Dionex model AS3500 autosampler was used. Twenty-five microliter samples were introduced onto a Dionex 4×250 mm OmniPac™ PAX-100 column. Dionex 4×50 mm OmniPac™ PAX-100 guard and ATC-1 anion trap columns were used. Inositol phosphates were eluted at 1 ml min$^{-1}$ with the following mobile phase gradient: 68% A (distilled water)/30% B (200 mM NaOH) for 4.0 min, 39% A/59% B at 4.1 through 15.0 min, return to initial conditions at 15.1 min. The mobile phase contained 2% C (50% aqueous isopropanol) at all times to maintain column performance. A Dionex conductivity detector module II was used with a Dionex ASRS-Ultra II anion self-regenerating suppressor set up in the external water mode and operated with a current of 300 mA. Although quantitative standards were available, $InsP_3$, $InsP_4$ and $InsP_5$ were partially but clearly resolved from each other and $InsP_6$.

Each plant identified as a potential high available phosphorus transgenic is tested again to confirm the original elevated phosphorus reading. Confirmed high-availability phosphorous lines are selected on the basis of uniformity for the trait. Transformants which are positive with the colorimetric assays can then be subjected to more rigorous analyses to include Southern, Northern and Western blotting and/or quantitation and identification of phytic acid and inositol phosphate intermediates by HPLC.

EXAMPLE 8

Stacking IP2K with Other Inositol Phosphate Kinase Genes

Figure 5:
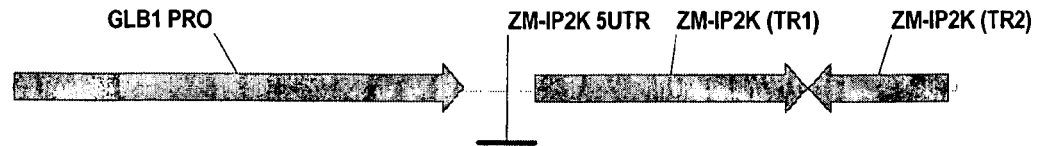
FIG. 5 shows a diagram of the plasmids described in Example 8.
Figure 5:
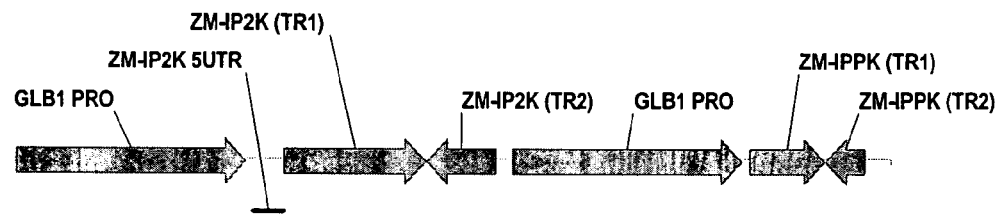
Figure 5:
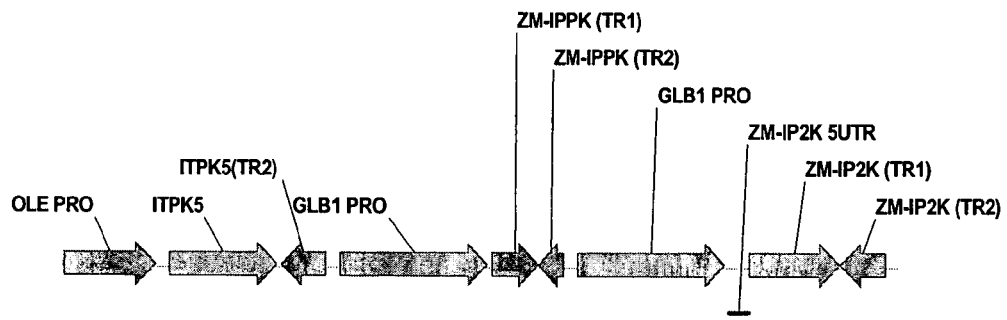

By "stacking" (i.e., transforming a plant with) constructs designed to reduce or eliminate the expression of IP2K and other proteins, it is expected that the reduction of phytic acid and increase in available phosphorus will be enhanced in comparison to plants transformed with constructs designed to reduce or eliminate the expression of IP2K alone. Accordingly, three constructs are made in which a Glb1 promoter is operably linked to an IP2K hairpin construct and an appropriate terminator. Two of the constructs additionally contain a Glb1 promoter operably linked to an IPPK hairpin construct, and one of these constructs further contains an Ole promoter operably linked to an ITPK-5 hairpin construct. These constructs are set forth in SEQ ID NOs: 10, 11, and 12, and are diagrammed in FIG. 5. The constructs are transformed into plant cells and transgenic plants are regenerated. These plants are assayed for phytate content.

EXAMPLE 9

Transgenic Maize Seeds Have Reduced Phytic Acid Content

Figure 6:
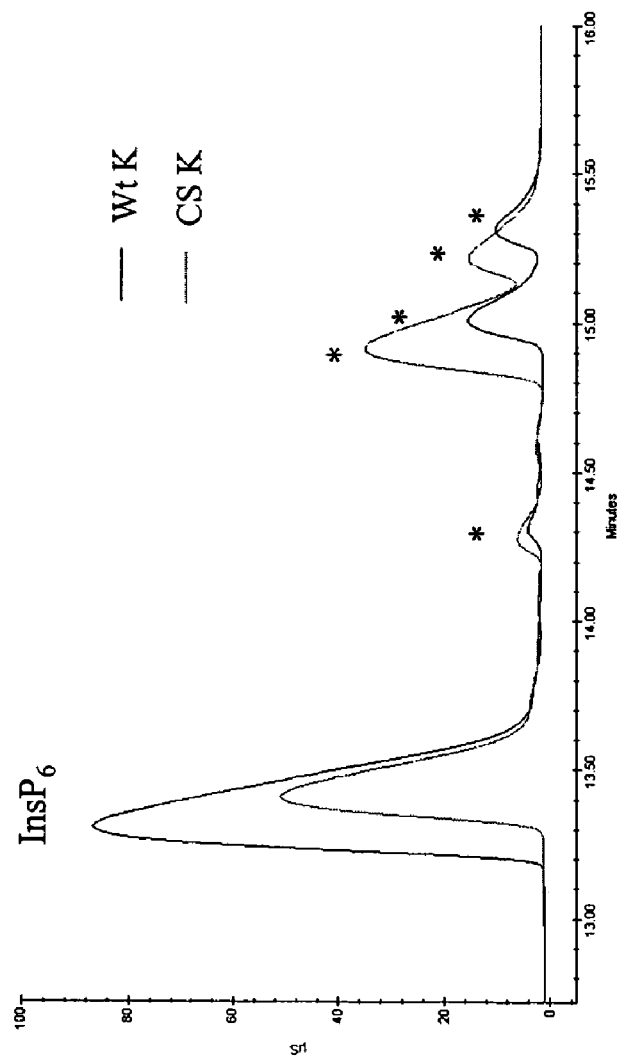
FIG. 6 shows results from HPLC analysis of IP2K transgenic seeds (see Example 9). These results demonstrate that phytic acid (InsP6) is reduced in IP2K transgenic seeds and the transgenic seeds accumulate myo-inositol phosphate intermediates. Asterisks (*) indicate uncharacterized myo-inositol phosphate intermediates. Briefly, IP2K cosuppression events were screened using a rapid $P_i$ assay method as described in Example 7, part A. For each cosuppression event, individual kernels were analyzed for Pi and phytic acid contents as described in Example 7, part B. Three wild-type kernels were pooled into a "wild-type group" and three cosuppression kernels were pooled into a separate group; the two pools of kernels were subjected to HPLC analysis as described in Example 7, part C.

A construct comprising IP2K operably linked to a Glb promoter ("Glb::IP2K") was used for maize transformation. Transgenic plants were obtained that represented 54 separate transformation events, and the seeds of those transgenic plants (T1 seeds) were analyzed for Pi and phytate content. This analysis showed that 11 of the 54 separate transformation events resulted in transgenic plants that had a significant increase in Pi in their seeds. Further analysis demonstrated that the phytate content in these seeds is reduced by 30 to 70% (see Table 1 below), confirming that the transformation of plants with the Glb::IP2K construct resulted in cosuppression of the IP2K gene. HPLC analysis of seed extracts confirmed that IP2K transgenic seeds accumulate myo-inositol phosphate intermediates (FIG. 6), as expected.

TABLE 1

Analysis of IP2K Transgenic Maize Seeds

| Event | Wt-K PAP | CS-K PAP | PA reduction |
|---|---|---|---|
| 1 | 2.25 | 1.51 | 33% |
| 2 | 1.63 | 0.99 | 39% |
| 3 | 2.19 | 0.93 | 58% |
| 4 | 2.47 | 0.73 | 70% |

(Wt-K, wild-type kernel;
CS-K, cosuppression kernel;
PAP, phytic acid phosphorus;
PA, phytic acid)

Wild-type kernals as indicated above were kernels in a segregation ear without the IP2K transgene and cosuppression kernels were the kernels in the same segregation ear that did contain the IP2K transgene. The PAP values in Table 1 were measured using the HPLC method outlined in Example 7.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for producing food or feed with a reduced amount of phytate, said method comprising:
   a) transforming a maize plant with a nucleic acid comprising a nucleotide sequence selected from the group consisting of:
      i) a nucleotide sequence having at least 95% sequence identity to the nucleotide sequence set forth in SEQ ID NO:15; and
      ii) a nucleotide sequence which is the complement of (i);
   b) growing said maize plant under conditions in which said nucleotide sequence is expressed, wherein expression of said nucleotide sequence inhibits or reduces the expression of IP2K-1; and
   c) producing food or feed from said maize plant,
   wherein said food or feed produced from said maize plant has a reduced amount of phytate in comparison to a maize plant that was not transformed with said nucleic acid.

2. The method of claim 1, wherein said nucleotide sequence is set forth in SEQ ID NO: 15 or is the complement of the nucleotide sequence set forth in SEQ ID NO: 15.

3. A transformed maize plant comprising in its genome at least one stably incorporated nucleic acid having a nucleotide sequence operably linked to a promoter that drives expression in said maize plant, wherein said nucleotide sequence is selected from the group consisting of:
   a) a nucleotide sequence having at least 95% sequence identity to the nucleotide sequence set forth in SEQ ID NO:15; and
   b) a nucleotide sequence which is the complement of (a);
   wherein expression of said nucleotide sequence inhibits or reduces the expression of IP2K-1, and wherein said maize plant has a reduced level of phytate compared to a maize plant not transformed with said nucleic acid.

4. The transformed maize plant of claim 3, wherein said nucleotide sequence comprises the nucleotide sequence set forth in SEQ ID NO: 15 or the complement of the nucleotide sequence set forth in SEQ ID NO:15.

5. Transformed seed of the maize plant of claim 3, wherein said seed comprises said nucleotide sequence.

* * * * *

UNITED STATES PATENT AND TRADEMARK OFFICE
CERTIFICATE OF CORRECTION

| | | |
|---|---|---|
| PATENT NO. | : 7,714,187 B2 | Page 1 of 1 |
| APPLICATION NO. | : 11/054168 | |
| DATED | : May 11, 2010 | |
| INVENTOR(S) | : Shi et al. | |

It is certified that error appears in the above-identified patent and that said Letters Patent is hereby corrected as shown below:

Column 16, line 42, "fonnamide" should be --formamide--;

Column 22, line 4, "amnmonium" should be --ammonium--;

Column 31, line 14, "Aroo" should be --$A_{600}$--; and

Column 40, line 48, "kernals" should be --kernels--.

Signed and Sealed this
Twenty-eighth Day of June, 2011

David J. Kappos
*Director of the United States Patent and Trademark Office*

SEQUENCE LISTING

<160> NUMBER OF SEQ ID NOS: 21

<210> SEQ ID NO 1
<211> LENGTH: 35
<212> TYPE: PRT
<213> ORGANISM: Artificial Sequence
<220> FEATURE:
<223> OTHER INFORMATION: Domain A consensus sequence
<220> FEATURE:
<221> NAME/KEY: VARIANT
<222> LOCATION: 6, 16
<223> OTHER INFORMATION: Can be Val or Ile
<220> FEATURE:
<221> NAME/KEY: VARIANT
<222> LOCATION: 8
<223> OTHER INFORMATION: Can be Lys or Arg
<220> FEATURE:
<221> NAME/KEY: VARIANT
<222> LOCATION: 12
<223> OTHER INFORMATION: Can be Ala or Gly
<220> FEATURE:
<221> NAME/KEY: VARIANT
<222> LOCATION: 18
<223> OTHER INFORMATION: Can be Ala or Ser
<220> FEATURE:
<221> NAME/KEY: VARIANT
<222> LOCATION: 20
<223> OTHER INFORMATION: Can be Thr or Ala
<220> FEATURE:
<221> NAME/KEY: VARIANT
<222> LOCATION: (26)...(26)
<223> OTHER INFORMATION: Can be Met or Phe
<220> FEATURE:
<221> NAME/KEY: VARIANT
<222> LOCATION: (27)...(27)
<223> OTHER INFORMATION: Can be Leu, Ile, or Val
<220> FEATURE:
<221> NAME/KEY: VARIANT
<222> LOCATION: (30)...(30)
<223> OTHER INFORMATION: Can be Val or Met
<220> FEATURE:
<221> NAME/KEY: VARIANT
<222> LOCATION: (31)...(31)
<223> OTHER INFORMATION: Can be Leu, Ile, or Met
<220> FEATURE:
<221> NAME/KEY: VARIANT
<222> LOCATION: (33)...(33)
<223> OTHER INFORMATION: Can be Leu, Ile, or Val
<220> FEATURE:
<221> NAME/KEY: VARIANT
<222> LOCATION: (34)...(34)
<223> OTHER INFORMATION: Can be Lys or Gln
<220> FEATURE:
<221> NAME/KEY: VARIANT
<222> LOCATION: (3)...(3)
<223> OTHER INFORMATION: Xaa can be any amino acid
<220> FEATURE:
<221> NAME/KEY: VARIANT
<222> LOCATION: (25)...(25)
<223> OTHER INFORMATION: Xaa can be any amino acid

<400> SEQUENCE: 1

Asp Ala Xaa Asp Trp Xaa Tyr Xaa Gly Glu Gly Xaa Ala Asn Leu Xaa
 1               5                  10                  15

Leu Xaa Tyr Xaa Gly Ser Ser Pro Xaa Xaa Xaa Gly Lys Xaa Xaa Arg
            20                  25                  30

Xaa Xaa Lys
        35

<210> SEQ ID NO 2
<211> LENGTH: 90
<212> TYPE: PRT

-continued

```
<213> ORGANISM: Artificial Sequence
<220> FEATURE:
<223> OTHER INFORMATION: Domain B consensus sequence
<220> FEATURE:
<221> NAME/KEY: VARIANT
<222> LOCATION: 2, 25
<223> OTHER INFORMATION: Can be Ile or Leu
<220> FEATURE:
<221> NAME/KEY: VARIANT
<222> LOCATION: 3, 70
<223> OTHER INFORMATION: Can be Ala or Ser
<220> FEATURE:
<221> NAME/KEY: VARIANT
<222> LOCATION: 15, 30, 73
<223> OTHER INFORMATION: Can be Ser or Thr
<220> FEATURE:
<221> NAME/KEY: VARIANT
<222> LOCATION: 18, 32, 72
<223> OTHER INFORMATION: Can be Tyr or Phe
<220> FEATURE:
<221> NAME/KEY: VARIANT
<222> LOCATION: 29, 64, 68, 81
<223> OTHER INFORMATION: Can be Ile or Val
<220> FEATURE:
<221> NAME/KEY: VARIANT
<222> LOCATION: (8)...(8)
<223> OTHER INFORMATION: Can be Ala or Pro
<220> FEATURE:
<221> NAME/KEY: VARIANT
<222> LOCATION: (13)...(13)
<223> OTHER INFORMATION: Can be Leu or Val
<220> FEATURE:
<221> NAME/KEY: VARIANT
<222> LOCATION: (21)...(21)
<223> OTHER INFORMATION: Can be Lys or Glu
<220> FEATURE:
<221> NAME/KEY: VARIANT
<222> LOCATION: (22)...(22)
<223> OTHER INFORMATION: Can be Asp or Glu
<220> FEATURE:
<221> NAME/KEY: VARIANT
<222> LOCATION: (28)...(28)
<223> OTHER INFORMATION: Can be Gln or Ser
<220> FEATURE:
<221> NAME/KEY: VARIANT
<222> LOCATION: (40)...(40)
<223> OTHER INFORMATION: Can be Phe or Leu
<220> FEATURE:
<221> NAME/KEY: VARIANT
<222> LOCATION: (43)...(43)
<223> OTHER INFORMATION: Can be Gly or Asn
<220> FEATURE:
<221> NAME/KEY: VARIANT
<222> LOCATION: (47)...(47)
<223> OTHER INFORMATION: Can be Lys or Glu
<220> FEATURE:
<221> NAME/KEY: VARIANT
<222> LOCATION: (52)...(52)
<223> OTHER INFORMATION: Can be Asp or Asn
<220> FEATURE:
<221> NAME/KEY: VARIANT
<222> LOCATION: (71)...(71)
<223> OTHER INFORMATION: Can be Leu or Phe
<220> FEATURE:
<221> NAME/KEY: VARIANT
<222> LOCATION: (83)...(83)
<223> OTHER INFORMATION: Can be Val or Leu
<220> FEATURE:
<221> NAME/KEY: VARIANT
<222> LOCATION: (88)...(88)
<223> OTHER INFORMATION: Can be Val, Ile, or Ala
<220> FEATURE:
<221> NAME/KEY: VARIANT
<222> LOCATION: 17, 24, 37, 41, 42, 48, 65, 66, 89
<223> OTHER INFORMATION: Can be any amino acid

<400> SEQUENCE: 2

Cys Xaa Xaa Val Glu Ile Lys Xaa Lys Cys Gly Phe Xaa Pro Xaa Ser
```

```
                1               5                  10                 15
Xaa Xaa Ile Ser Xaa Xaa Asn Xaa Xaa Lys Lys Xaa Xaa Xaa Arg Xaa
                    20                 25                 30

Lys Met His Gln Xaa Leu Lys Xaa Xaa Xaa Glu Ile Ser Xaa Xaa
                    35                 40                 45

Ser Glu Tyr Xaa Pro Leu Asp Leu Phe Ser Gly Ser Lys Glu Arg Xaa
        50                 55                 60

Xaa Xaa Ala Xaa Lys Xaa Xaa Xaa Thr Pro Gln Asn Asn Phe Arg
65                  70                 75                 80

Xaa Phe Xaa Asn Gly Ser Leu Xaa Xaa Gly
                85                 90

<210> SEQ ID NO 3
<211> LENGTH: 33
<212> TYPE: PRT
<213> ORGANISM: Artificial Sequence
<220> FEATURE:
<223> OTHER INFORMATION: Domain C consensus sequence
<220> FEATURE:
<221> NAME/KEY: VARIANT
<222> LOCATION: 5
<223> OTHER INFORMATION: Can be Gly or Asp
<220> FEATURE:
<221> NAME/KEY: VARIANT
<222> LOCATION: 6, 9, 10, 15, 16, 24, 27, 28, 30
<223> OTHER INFORMATION: Can be any amino acid

<400> SEQUENCE: 3

Ser Gly Val Leu Xaa Xaa Leu Leu Xaa Xaa Gln Lys Leu Asp Xaa Xaa
1               5                  10                 15

Asp Ile Glu Gly Ala Ile His Xaa Tyr Tyr Xaa Xaa Ile Xaa Gln Pro
                20                 25                 30

Cys

<210> SEQ ID NO 4
<211> LENGTH: 31
<212> TYPE: PRT
<213> ORGANISM: Artificial Sequence
<220> FEATURE:
<223> OTHER INFORMATION: Domain D consensus sequence
<220> FEATURE:
<221> NAME/KEY: VARIANT
<222> LOCATION: 1, 6
<223> OTHER INFORMATION: Can be Leu or Met
<220> FEATURE:
<221> NAME/KEY: VARIANT
<222> LOCATION: 4
<223> OTHER INFORMATION: Can be Leu or Ile
<220> FEATURE:
<221> NAME/KEY: VARIANT
<222> LOCATION: 8
<223> OTHER INFORMATION: Can be Lys or Glu
<220> FEATURE:
<221> NAME/KEY: VARIANT
<222> LOCATION: 13
<223> OTHER INFORMATION: Can be Val or Leu
<220> FEATURE:
<221> NAME/KEY: VARIANT
<222> LOCATION: 14
<223> OTHER INFORMATION: Can be Lys or Arg
<220> FEATURE:
<221> NAME/KEY: VARIANT
<222> LOCATION: (16)...(16)
<223> OTHER INFORMATION: Can be Phe or Tyr
<220> FEATURE:
<221> NAME/KEY: VARIANT
<222> LOCATION: (19)...(19)
<223> OTHER INFORMATION: Can be Ser or Ala
<220> FEATURE:
```

```
<221> NAME/KEY: VARIANT
<222> LOCATION: (27)...(27)
<223> OTHER INFORMATION: Can be Ile, Leu, or Val
<220> FEATURE:
<221> NAME/KEY: VARIANT
<222> LOCATION: (10)...(10)
<223> OTHER INFORMATION: Can be any amino acid
<220> FEATURE:
<221> NAME/KEY: VARIANT
<222> LOCATION: (15)...(15)
<223> OTHER INFORMATION: Can be any amino acid

<400> SEQUENCE: 4

Xaa His Ser Xaa Pro Xaa Asp Xaa Ser Xaa Lys Ile Xaa Xaa Xaa
 1               5                  10                  15

Leu Ile Xaa Ala Thr Ala Lys Asp Cys Ser Xaa Met Ile Ser Phe
             20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Domain E consensus sequence
<220> FEATURE:
<221> NAME/KEY: VARIANT
<222> LOCATION: 1, 22
<223> OTHER INFORMATION: Can be Phe or Tyr
<220> FEATURE:
<221> NAME/KEY: VARIANT
<222> LOCATION: 2
<223> OTHER INFORMATION: Can be Asp or Glu
<220> FEATURE:
<221> NAME/KEY: VARIANT
<222> LOCATION: 6
<223> OTHER INFORMATION: Can be Tyr or HIs
<220> FEATURE:
<221> NAME/KEY: VARIANT
<222> LOCATION: 8
<223> OTHER INFORMATION: Can be Ile, Leu, or Val
<220> FEATURE:
<221> NAME/KEY: VARIANT
<222> LOCATION: 12
<223> OTHER INFORMATION: Can be Val, Leu, or Met
<220> FEATURE:
<221> NAME/KEY: VARIANT
<222> LOCATION: (16)...(16)
<223> OTHER INFORMATION: Can be Asp or Lys
<220> FEATURE:
<221> NAME/KEY: VARIANT
<222> LOCATION: (26)...(26)
<223> OTHER INFORMATION: Can be Gln or Lys
<220> FEATURE:
<221> NAME/KEY: VARIANT
<222> LOCATION: (27)...(27)
<223> OTHER INFORMATION: Can be Lys or Arg
<220> FEATURE:
<221> NAME/KEY: VARIANT
<222> LOCATION: (29)...(29)
<223> OTHER INFORMATION: Can be Val, Ile, or Met
<220> FEATURE:
<221> NAME/KEY: VARIANT
<222> LOCATION: (0)...(0)
<223> OTHER INFORMATION: Amino acids at positions 5, 19, 20, and 31 can
      be any amino acid

<400> SEQUENCE: 5

Xaa Xaa Tyr Lys Xaa Xaa Phe Xaa Asp Leu Asp Xaa Lys Pro Leu Xaa
 1               5                  10                  15

Lys Met Xaa Xaa Tyr Xaa Lys Leu Asp Xaa Xaa Ile Xaa Asn Xaa Tyr
             20                  25                  30

<210> SEQ ID NO 6
```

```
<211> LENGTH: 451
<212> TYPE: PRT
<213> ORGANISM: Arabidopsis thaliana

<400> SEQUENCE: 6

Met Glu Met Ile Leu Glu Glu Lys Asp Ala Ser Asp Trp Ile Tyr Arg
 1               5                  10                  15

Gly Glu Gly Gly Ala Asn Leu Val Leu Ala Tyr Ala Gly Ser Ser Pro
             20                  25                  30

Leu Phe Val Gly Lys Val Ile Arg Ile Gln Lys Ala Arg Arg Asn Asp
         35                  40                  45

Lys Ala Ile Lys Asn Ala Asn Gly Val Val Ser Val Leu Thr Ser Asp
     50                  55                  60

Glu Gln His Leu Trp Arg Glu Asn Asn Glu Leu Ile Ser Ser Pro Asn
 65                  70                  75                  80

Lys Glu Val Leu Glu Gln Arg Tyr Val Lys Asn Val Ile Ile Pro Leu
                 85                  90                  95

Leu Gly Pro Lys His Val Asp Ala Gly Val Arg Val Ser Val Ser Lys
            100                 105                 110

Glu Phe Leu Glu Cys Val Asp Lys Lys Val Thr Lys Gln Arg Pro Leu
        115                 120                 125

Trp Arg Val Asn Ala Ala Asn Val Asp Thr Ser His Asp Ser Ala Leu
    130                 135                 140

Ile Leu Asn Asp His Ser Leu Phe Ser Gln Gly Ile Ser Ser Gly Gly
145                 150                 155                 160

Asp Cys Ile Ser Val Glu Ile Lys Pro Lys Cys Gly Phe Leu Pro Thr
                165                 170                 175

Ser Arg Phe Ile Gly Lys Glu Asn Met Leu Lys Thr Ser Val Ser Arg
            180                 185                 190

Phe Lys Met His Gln Leu Leu Lys Leu Glu Tyr Asn Glu Ile Ser Glu
        195                 200                 205

Glu Ser Glu Tyr Asp Pro Leu Asp Leu Phe Ser Gly Ser Lys Glu Ser
    210                 215                 220

Val Leu Glu Ala Ile Lys Ala Leu Tyr Ser Thr Pro Gln Asn Asn Phe
225                 230                 235                 240

Arg Val Phe Leu Asn Gly Ser Leu Ile Leu Gly Gly Ser Gly Glu Ser
                245                 250                 255

Thr Gly Arg Thr Ser Pro Glu Ile Gly Tyr Ala Phe Glu Asp Ala Leu
            260                 265                 270

Lys Gly Phe Ile Gln Ser Glu Asp Gly His Arg Thr Glu Cys Phe Leu
        275                 280                 285

Gln Leu Val Ser Asp Ala Val Tyr Gly Ser Gly Val Leu Asp Arg Leu
    290                 295                 300

Leu Glu Ile Gln Lys Leu Asp Lys Leu Asp Ile Glu Gly Ala Ile His
305                 310                 315                 320

Ser Tyr Tyr Asp Leu Ile Asn Gln Pro Cys Pro Ile Cys Lys Glu Gly
                325                 330                 335

Lys Pro Leu Glu Ala Glu Leu Ser Leu His Ala Leu Pro Leu Asp Glu
            340                 345                 350

Ser Leu Lys Ile Val Lys Glu Tyr Leu Ile Ala Ala Thr Ala Lys Asp
        355                 360                 365

Cys Ser Ile Met Ile Ser Phe Gln Ser Arg Asn Ala Trp Asp Ser Glu
    370                 375                 380

Pro Ser Gly Asp Tyr Val Ser Leu Lys Pro Thr Asn Gln Thr Phe Asp
```

```
                385                 390                 395                 400
Tyr Lys Val His Phe Ile Asp Leu Ser Leu Lys Pro Leu Lys Arg Met
                405                 410                 415
Glu Ser Tyr Tyr Lys Leu Asp Lys Lys Ile Ile Ser Phe Tyr Asn Arg
            420                 425                 430
Lys Gln Lys Ala Glu Asn Thr Ala Glu Gln Ile Gly Asn Ser Lys Pro
        435                 440                 445
Ser His Ser
    450

<210> SEQ ID NO 7
<211> LENGTH: 457
<212> TYPE: PRT
<213> ORGANISM: Arabidopsis thaliana

<400> SEQUENCE: 7

Met Glu Glu Ile Val Leu Glu Pro Lys Asp Ala Val Asp Trp Ser Tyr
 1               5                  10                  15
Arg Gly Glu Gly Ala Val Asn Leu Val Leu Ala Tyr Thr Gly Ser Ser
            20                  25                  30
Pro Ser Phe Leu Gly Lys Met Met Arg Ile Gln Lys Met Pro Lys Asp
        35                  40                  45
Gly Asn Glu Asn Gly Asp Lys Ser Glu Asn Gly Leu Thr Thr His Glu
    50                  55                  60
Lys Leu Ile Trp Gly Asp Val Lys Asp Leu Val Ser Cys Lys Asn Lys
65                  70                  75                  80
Glu Ile Glu Glu Tyr Leu Phe Val Lys His Val Met Arg Pro Leu Leu
                85                  90                  95
Gly Arg Lys His Val Asn Pro Gly Val Cys Phe Leu Phe Ile Ser Phe
            100                 105                 110
Ser Cys His Asp Ser Asn Ala Met Ile Leu Leu Leu Val Ala Lys Glu
        115                 120                 125
Phe Leu Glu Ser Val Glu Lys Ile Ile Thr Ser Gln Arg Pro Ser Trp
    130                 135                 140
Arg Ala Asp Val Ala Ser Val Asp Thr Asn Arg Ser Ser Val Leu Leu
145                 150                 155                 160
Met Asp Asp Leu Thr Leu Phe Ala His Gly His Val Glu Asp Lys Pro
                165                 170                 175
Cys Leu Ser Val Glu Ile Lys Pro Lys Cys Gly Phe Leu Pro Ser Ser
            180                 185                 190
Ser Phe Ile Ala Glu Glu Asn Val Ile Lys Lys Ser Ile Thr Arg Phe
        195                 200                 205
Glu Met His Gln Val Leu Lys Leu Arg Glu Asn Glu Ile Ser Glu Ile
    210                 215                 220
Ser Glu Tyr Asp Pro Leu Asp Leu Phe Ser Gly Ser Lys Glu Arg Ile
225                 230                 235                 240
Leu Glu Ala Ile Lys Ala Leu Tyr Thr Thr Pro Gln Asn Asn Phe Arg
                245                 250                 255
Val Phe Leu Asn Gly Ser Leu Val Phe Gly Gly Leu Gly Gly Gly Ile
            260                 265                 270
Cys Lys Thr Thr Ser Lys Val Glu Leu Ala Phe Glu His Ile Leu Lys
        275                 280                 285
Asp Ile Ile Lys Thr Asp Asp Gly Leu Arg Ala Asp Arg Phe Ile Glu
    290                 295                 300
```

```
Leu Val Ala Glu Thr Val Tyr Thr Ser Gly Val Leu Asp Gln Leu Leu
305                 310                 315                 320

Asp Val Gln Lys Leu Asp Arg Tyr Asn Ile Glu Gly Ala Ile His Val
            325                 330                 335

Tyr Tyr Asp Phe Ile Asp Gln Pro Cys Lys Val Cys Arg Glu Leu Asn
            340                 345                 350

Gln Phe Ser Ser Met His Ser Ile Pro Met Asp Glu Lys Val Asn Ile
            355                 360                 365

Leu Lys Glu Phe Leu Ile Ser Ala Thr Ala Lys Asp Cys Ser Val Met
    370                 375                 380

Ile Ser Phe Arg Ser Thr Glu Ala Gly Leu Ser Lys Ser Ser Ser His
385                 390                 395                 400

Ser Asn Leu His Leu Glu Thr Thr Lys Gln Glu Phe Glu Tyr Lys Val
            405                 410                 415

His Phe Ile Asp Leu Asp Met Arg Pro Leu Lys Lys Met Glu Val Tyr
            420                 425                 430

Tyr Glu Leu Asp Lys Lys Ile Met Asn Thr Tyr Leu Glu Met Leu Lys
            435                 440                 445

Lys Lys Gly Thr Gln Pro Gln Cys Leu
    450                 455

<210> SEQ ID NO 8
<211> LENGTH: 288
<212> TYPE: PRT
<213> ORGANISM: Brassica napus

<400> SEQUENCE: 8

Met Ile Leu Glu Glu Lys Asp Ala Ser Asp Trp Ile Tyr Arg Gly Glu
1               5                   10                  15

Gly Gly Ala Asn Leu Val Leu Ala Tyr Ala Ala Ser Ser Pro Leu Phe
            20                  25                  30

Val Gly Lys Val Ile Arg Ile Gln Lys Ala Pro Lys Thr Asp Lys Ala
        35                  40                  45

Asn Lys Ala Val Asn Gly Ala Ala Ser Val Leu Thr Thr Asp Glu Gln
    50                  55                  60

Leu Leu Trp Arg Glu Asn Lys Glu Leu Val Ser Ser Pro Asn Lys Glu
65                  70                  75                  80

Val Val Glu Gln Ile Tyr Val Lys Asp Val Ile Pro Leu Leu Gly
                85                  90                  95

Pro Lys His Ile Asp Pro Gly Val Arg Val Ser Val Ser Lys Glu Phe
            100                 105                 110

Leu Glu Ser Val Asp Lys Lys Val Thr Lys Gln Arg Pro Pro Trp Arg
        115                 120                 125

Val Asn Ala Ala Asn Val Asp Thr Ser His Asp Ser Ala Leu Ile Leu
    130                 135                 140

Asn Asp His Ser Leu Phe Ser Gln Gly Ile Ser Ser Gly Asp Cys Leu
145                 150                 155                 160

Ser Val Glu Ile Lys Pro Lys Cys Gly Phe Leu Pro Thr Ser Arg Phe
                165                 170                 175

Ile Ser Glu Glu Asn Lys Leu Lys Arg Ser Val Ser Arg Phe Lys Met
            180                 185                 190

His Gln Ile Leu Lys Leu Glu Arg Asn Glu Ile Ser Glu Val Ser Glu
        195                 200                 205

Tyr Asp Pro Leu Asp Leu Phe Ser Gly Ser Lys Asp Arg Val Ser Lys
    210                 215                 220
```

```
Ala Val Lys Ala Leu Tyr Ser Ile Pro Gln Asn Asn Phe Arg Val Phe
225                 230                 235                 240

Leu Asn Gly Ser Leu Val Leu Gly Gly Ser Gly Glu Ser Thr Gly Arg
            245                 250                 255

Thr Ser Pro Glu Leu His Arg Pro Leu Arg Ser Thr Gln Arg Leu His
            260                 265                 270

Pro Ile Lys Arg Trp Ser Gln Asp Lys Met Leu Ser Thr Ala Ser Asn
            275                 280                 285

<210> SEQ ID NO 9
<211> LENGTH: 445
<212> TYPE: PRT
<213> ORGANISM: Oryza sativa

<400> SEQUENCE: 9

Met Glu Val Val Leu His Glu Gly Asp Ala Lys Asp Trp Val Tyr Lys
1               5                   10                  15

Gly Glu Gly Ala Ala Asn Leu Ile Leu Ser Tyr Thr Gly Ser Ser Pro
            20                  25                  30

Ser Met Leu Gly Lys Val Leu Arg Val Lys Lys Ile Leu Lys Asp Lys
        35                  40                  45

Gly Gln Pro Ala Pro Asn Cys Ile Val Phe Ser Ser His Glu Glu His
    50                  55                  60

Leu Trp Gly Lys Ile Pro Gly Leu Leu Glu Ser Val Lys Asn Asp Cys
65              70                  75                  80

Leu Pro Gln Ala Tyr Ala Thr Ile Val Met Ser Gln His Leu Gly Ala
                85                  90                  95

Asn His Val Asp Gly Gly Val Arg Val Arg Val Ser Lys Asn Phe Phe
            100                 105                 110

Glu Leu Ala Gly Lys Asn Val Leu Asp Asn Arg Pro Ala Trp Arg Val
        115                 120                 125

Asn Ala Ser Ala Ile Asp Ala Gly Ala Asp Ser Ala Leu Leu Ile Ser
    130                 135                 140

Asp His Thr Leu Phe Ser Gly Asn Pro Arg Gly Ser Ser Cys Ile Ala
145                 150                 155                 160

Val Glu Ile Lys Ala Lys Cys Gly Phe Leu Pro Ser Ser Glu Tyr Ile
                165                 170                 175

Ser Lys Glu Asn Ser Ile Lys Lys Gln Val Thr Arg Tyr Lys Met His
            180                 185                 190

Gln His Leu Lys Phe His Leu Gly Glu Ile Ser Lys Thr Ser Glu Tyr
        195                 200                 205

Asp Pro Leu Asp Leu Phe Ser Gly Ser Lys Glu Arg Ile His Met Ala
    210                 215                 220

Ile Lys Ser Phe Phe Ser Thr Pro Gln Asn Asn Phe Arg Ile Phe Val
225                 230                 235                 240

Asp Gly Ser Leu Val Phe Gly Gly Met Gly Gly Ala Asp Ser Val
                245                 250                 255

His Pro Asn Glu Thr Glu Lys Cys Leu Glu Asp Leu Ser Lys Val Thr
            260                 265                 270

Gly Leu Gln Leu Ser Asp Phe Ile Glu Leu Leu Ser Glu Ala Ile Phe
        275                 280                 285

Lys Ser Gly Val Leu Gly Lys Leu Leu Ala Thr Gln Lys Leu Asp Asp
    290                 295                 300

His Asp Ile Glu Gly Ala Ile His Leu Tyr Tyr Asn Ile Ile Ser Gln
```

```
305                 310                 315                 320
Pro Cys Leu Val Cys Lys Ser Ile Thr Asp Thr Glu Leu Leu Arg Lys
                325                 330                 335

Tyr Ser Thr Leu His Ser Leu Pro Leu Asp Lys Ser Glu Lys Ile Val
            340                 345                 350

Arg Asp Phe Leu Ile Ser Ala Thr Ala Lys Asp Cys Ser Leu Met Ile
                355                 360                 365

Ser Phe Arg Pro Arg Gln Ser Gly Thr Thr Asp Ser Glu Tyr Asp Ser
    370                 375                 380

Val Phe Leu Asp Ser Val Asn Gln Ser Tyr Asp Tyr Lys Ala Tyr Phe
385                 390                 395                 400

Ile Asp Leu Asp Val Lys Pro Leu Asp Lys Met Val His Tyr Phe Lys
                405                 410                 415

Leu Asp Gln Lys Ile Val Asn Phe Tyr Thr Arg Asn Gly Glu Val Gly
            420                 425                 430

Gly Asp Pro Arg Asp Pro Pro Lys Gly Cys Gly Pro Arg
        435                 440                 445

<210> SEQ ID NO 10
<211> LENGTH: 2940
<212> TYPE: DNA
<213> ORGANISM: Artificial Sequence
<220> FEATURE:
<223> OTHER INFORMATION: plasmid PHP 20588
<220> FEATURE:
<221> NAME/KEY: promoter
<222> LOCATION: (1)...(1402)
<223> OTHER INFORMATION: Glb1 promoter
<220> FEATURE:
<221> NAME/KEY: 5'UTR
<222> LOCATION: (1447)...(1627)
<223> OTHER INFORMATION: Zea mays IP2K 5' UTR
<220> FEATURE:
<221> NAME/KEY: misc_RNA
<222> LOCATION: (1628)...(2479)
<223> OTHER INFORMATION: first 847 bp of Zea mays IP2K gene
<220> FEATURE:
<221> NAME/KEY: misc_RNA
<222> LOCATION: (2480)...(2912)
<223> OTHER INFORMATION: complement of 431 bp fragment of Zea mays IP2K
      gene

<400> SEQUENCE: 10
agcttgccga gtgccatcct tggacactcg ataaagtata ttttattttt tttattttgc      60
caaccaaact ttttgtggta tgttcctaca ctatgtagat ctacatgtac cattttggca    120
caattacata tttacaaaaa tgttttctat aaatattaga tttagttcgt ttatttgaat    180
ttcttcggaa aattcacatt taaactgcaa gtcactcgaa acatggaaaa ccgtgcatgc    240
aaaataaatg atatgcatgt tatctagcac aagttacgac cgatttcaga agcagaccag    300
aatcttcaag caccatgctc actaaacatg accgtgaact tgttatctag ttgtttaaaa    360
attgtataaa acacaaataa agtcagaaat taatgaaact tgtccacatg tcatgatatc    420
atatatagag gttgtgataa aaatttgata atgtttcggt aaagttgtga cgtactatgt    480
gtagaaacct aagtgaccta cacataaaat catagagttt caatgtagtt cactcgacaa    540
agactttgtc aagtgtccga taaaagtac tcgacaaaga agccgttgtc gatgtactgt    600
tcgtcgagat ctctttgtcg agtgtcacac taggcaaagt ctttacggag tgtttttcag    660
gctttgacac tcggcaaagc gctcgattcc agtagtgaca gtaatttgca tcaaaaatag    720
ctgagagatt taggccccgt ttcaatctca cgggataaag tttagcttcc tgctaaactt    780
```

```
tagctatatg aattgaagtg ctaaagttta gtttcaatta ccaccattag ctctcctgtt      840
tagattacaa atggctaaaa gtagctaaaa aatagctgct aaagtttatc tcgcgagatt      900
gaaacagggc cttaaaatga gtcaactaat agaccaacta attattagct attagtcgtt      960
agcttcttta atctaagcta aaccaacta atagcttatt tgttgaatta caattagctc     1020
aacggaattc tctgtttttc taaaaaaaaa ctgcccctct cttacagcaa attgtccgct     1080
gcccgtcgtc cagatacaat gaacgtacct agtaggaact cttttacacg ctcggtcgct     1140
cgccgcggat cggagtcccc ggaacacgac accactgtgg aacacgacaa agtctgctca     1200
gaggcggcca caccctggcg tgcaccgagc cggagcccgg ataagcacgg taaggagagt     1260
acggcgggac gtggcgaccc gtgtgtctgc tgccacgcag ccttcctcca cgtagccgcg     1320
cggccgcgcc acgtaccagg gcccggcgct ggtataaatg cgcgccacct ccgctttagt     1380
tctgcataca gccaacccaa ggatccaaca cacacccgag gatatcacag tcgacccacg     1440
cgtccgagca ccagcatctc ttcaggtctc caccaagcgc agacaccgca gcagcggcag     1500
cggcacgatc tggtgacccc ccgccgcgt caagcctgct cctccggtga tcgccggact     1560
ggcggggtag gaaccagcgg agcgcagccc gcctccttcc gctgtgtctg acagcagcag     1620
atcctcgatg gagatggatg gggttctgca agccgcggat gccaaggatt gggtttacaa     1680
gggggaaggc gccgcgaatc ttatcctcag ctacaccggc tcgtcgccct ccatgcttgg     1740
caaggtactg cggctcaaga agattctaaa aaacaagtcg cagcgggcac caagttgtat     1800
tgtattctca agtcatgagc aactcctgtg gggccatatc ccagaactgg ttgagtcggt     1860
caaacaagat tgcttggctc aagcctatgc agtgcatgtt atgagccaac acctgggtgc     1920
caatcatgtc gatggtgggg tccgtgtacg tgttctagg gattttctgg agcttgtcga     1980
aaagaatgtt cttagcagcc gtcctgctgg gagagtaaat gcaagttcaa ttgataacac     2040
tgctgatgcc gctcttctga tagcagacca ctctttattt tctggcaatc ctaagggtag     2100
cagctgcata gctgtagaga taaaggccaa atgtgggttt ctgccatcat cagaatatat     2160
atcagaagat aatactatca agaaacaagt aacgagatat aagatgcatc agcacctcaa     2220
attttatcag ggtgagatat cgaagactag tgagtacaat cctcttgatc tattttctgg     2280
gtcaaaagag agaatatgca tggccatcaa gtccctttc tcaactcctc agaacaactt     2340
aaggattttt gtcaatggat cttagctttt tggtggcatg ggaggtggtg cagatagtgt     2400
tcatcctgct gacactctta agtgtcttga agatctcagc aagattagtg gcctaaaact     2460
ccctgacttc actgagctct cgttacttgt ttcttgatag tattatcttc tgatatatat     2520
tctgatgatg gcagaaaccc acatttggcc tttatctcta cagctatgca gctgctaccc     2580
ttaggattgc cagaaaataa agagtggtct gctatcagaa gagcggcatc agcagtgtta     2640
tcaattgaac ttgcatttac tctcccagca ggacggctgc taagaacatt cttttcgaca     2700
agctccagaa aatccctaga aacacgtaca cggaccccac catcgacatg attggcaccc     2760
aggtgttggc tcataacatg cactgcatag gcttgagcca agcaatcttg tttgaccgac     2820
tcaaccagtt ctgggatatg gccccacagg agttgctcat gacttgagaa tacaatacaa     2880
cttggtgccc gctgcgactt gttttttaga aagcttcggt ccgaagcttg catgcctgca     2940
```

<210> SEQ ID NO 11
<211> LENGTH: 5303
<212> TYPE: DNA
<213> ORGANISM: Artificial Sequence
<220> FEATURE:
<223> OTHER INFORMATION: plasmid PHP 21330

```
<220> FEATURE:
<221> NAME/KEY: promoter
<222> LOCATION: (1)...(1402)
<223> OTHER INFORMATION: Glb1 promoter
<220> FEATURE:
<221> NAME/KEY: 5'UTR
<222> LOCATION: (1447)...(1627)
<223> OTHER INFORMATION: Zea mays IP2K 5' UTR
<220> FEATURE:
<221> NAME/KEY: misc_RNA
<222> LOCATION: (1628)...(2479)
<223> OTHER INFORMATION: first 847 bp of Zea mays IP2K gene
<220> FEATURE:
<221> NAME/KEY: misc_RNA
<222> LOCATION: (2480)...(2911)
<223> OTHER INFORMATION: complement of fragment of Zea mays IP2K gene
<220> FEATURE:
<221> NAME/KEY: promoter
<222> LOCATION: (3013)...(4414)
<223> OTHER INFORMATION: Glb1 promoter
<220> FEATURE:
<221> NAME/KEY: misc_RNA
<222> LOCATION: (4456)...(4907)
<223> OTHER INFORMATION: fragment of Zea mays IPPK gene
<220> FEATURE:
<221> NAME/KEY: misc_RNA
<222> LOCATION: (4909)...(5148)
<223> OTHER INFORMATION: complement of fragment of Zea mays IPPK gene

<400> SEQUENCE: 11
agcttgccga gtgccatcct tggacactcg ataaagtata ttttattttt tttattttgc      60
caaccaaact ttttgtggta tgttcctaca ctatgtagat ctacatgtac cattttggca     120
caattacata tttacaaaaa tgttttctat aaatattaga tttagttcgt ttatttgaat     180
ttcttcggaa aattcacatt taaactgcaa gtcactcgaa acatggaaaa ccgtgcatgc     240
aaaataaatg atatgcatgt tatctagcac aagttacgac cgatttcaga agcagaccag     300
aatcttcaag caccatgctc actaaacatg accgtgaact tgttatctag ttgtttaaaa     360
attgtataaa acacaaataa agtcagaaat taatgaaact tgtccacatg tcatgatatc     420
atatatagag gttgtgataa aaatttgata atgtttcggt aaagttgtga cgtactatgt     480
gtagaaacct aagtgaccta cacataaaat catagagttt caatgtagtt cactcgacaa     540
agactttgtc aagtgtccga taaaagtac tcgacaaaga agccgttgtc gatgtactgt      600
tcgtcgagat ctctttgtcg agtgtcacac taggcaaagt cttacggag tgttttcag      660 gctttgacac tcggcaaagc gctcgattcc agtagtgaca gtaatttgca tcaaaaatag     720
ctgagagatt taggccccgt ttcaatctca cgggataaag tttagcttcc tgctaaactt     780
tagctatatg aattgaagtg ctaaagttta gtttcaatta ccaccattag ctctcctgtt     840
tagattacaa atggctaaaa gtagctaaaa aatagctgct aaagtttatc tcgcgagatt     900
gaaacagggc cttaaaatga gtcaactaat agaccaacta attattagct attagtcgtt     960
agcttcttta atctaagcta aaaccaacta atagcttatt tgttgaatta caattagctc    1020
aacggaattc tctgtttttc taaaaaaaaa ctgcccctct cttacagcaa attgtccgct    1080
gcccgtcgtc cagatacaat gaacgtacct agtaggaact cttttacacg ctcggtcgct    1140
cgccgcggat cggagtcccc ggaacacgac accactgtgg aacacgacaa agtctgctca    1200
gaggcggcca caccctggcg tgcaccgagc cggagcccgg ataagcacgg taaggagagt    1260
acggcgggac gtggcgaccc gtgtgtctgc tgccacgcag ccttcctcca cgtagccgcg    1320
cggccgcgcc acgtaccagg gcccggcgct ggtataaatg cgcgccacct ccgctttagt    1380
tctgcataca gccaacccaa ggatccaaca cacacccgag gatatcacag tcgacccacg    1440
```

```
cgtccgagca ccagcatctc ttcaggtctc caccaagcgc agacaccgca gcagcggcag    1500
cggcacgatc tggtgacccc cccgccgcgt caagcctgct cctccggtga tcgccggact    1560
ggcggggtag gaaccagcgg agcgcagccc gcctccttcc gctgtgtctg acagcagcag    1620
atcctcgatg gagatggatg gggttctgca agccgcggat gccaaggatt gggtttacaa    1680
gggggaaggc gccgcgaatc ttatcctcag ctacaccggc tcgtcgccct ccatgcttgg    1740
caaggtactg cggctcaaga agattctaaa aaacaagtcg cagcgggcac caagttgtat    1800
tgtattctca agtcatgagc aactcctgtg gggccatatc ccagaactgg ttgagtcggt    1860
caaacaagat tgcttggctc aagcctatgc agtgcatgtt atgagccaac acctgggtgc    1920
caatcatgtc gatggtgggg tccgtgtacg tgtttctagg gattttctgg agcttgtcga    1980
aaagaatgtt cttagcagcc gtcctgctgg gagagtaaat gcaagttcaa ttgataacac    2040
tgctgatgcc gctcttctga tagcagacca ctctttattt tctggcaatc ctaagggtag    2100
cagctgcata gctgtagaga taaaggccaa atgtgggttt ctgccatcat cagaatatat    2160
atcagaagat aatactatca agaaacaagt aacgagatat aagatgcatc agcacctcaa    2220
attttatcag ggtgagatat cgaagactag tgagtacaat cctcttgatc tattttctgg    2280
gtcaaaagag agaatatgca tggccatcaa gtccctttc tcaactcctc agaacaactt    2340
aaggattttt gtcaatggat ctttagcttt tggtggcatg ggaggtggtg cagatagtgt    2400
tcatcctgct gacactctta agtgtcttga agatctcagc aagattagtg gcctaaaact    2460
ccctgacttc actgagctct cgttacttgt ttccttgatag tattatcttc tgatatatat    2520
tctgatgatg gcagaaaccc acatttggcc tttatctcta cagctatgca gctgctaccc    2580
ttaggattgc cagaaaataa agagtggtct gctatcagaa gagcggcatc agcagtgtta    2640
tcaattgaac ttgcatttac tctcccagca ggacggctgc taagaacatt cttttcgaca    2700
agctccagaa aatccctaga aacacgtaca cggaccccac catcgacatg attggcaccc    2760
aggtgttggc tcataacatg cactgcatag gcttgagcca agcaatcttg tttgaccgac    2820
tcaaccagtt ctgggatatg gccccacagg agttgctcat gacttgagaa tacaatacaa    2880
cttggtgccc gctgcgactt gttttttaga aagcttcggt ccgggcctag aaggccagct    2940
tcaagtttgt acaaaaaagc aggctccggc cagaatggcc cggaccgggt tacccggacc    3000
ggaattcgat taagcttgcc gagtgccatc cttggacact cgataaagta tattttattt    3060
tttttatttt gccaaccaaa ctttttgtgg tatgttccta cactatgtag atctacatgt    3120
accattttgg cacaattaca tatttacaaa aatgttttct ataaatatta gatttagttc    3180
gtttatttga atttcttcgg aaaattcaca tttaaactgc aagtcactcg aaacatggaa    3240
aaccgtgcat gcaaaataaa tgatatgcat gttatctagc acaagttacg accgatttca    3300
gaagcagacc agaatcttca agcaccatgc tcactaaaca tgaccgtgaa cttgttatct    3360
agttgtttaa aaattgtata aaacacaaat aaagtcagaa attaatgaaa cttgtccaca    3420
tgtcatgata tcatatatag aggttgtgat aaaaatttga taatgtttcg gtaaagttgt    3480
gacgtactat gtgtagaaac ctaagtgacc tacacataaa atcatagagt ttcaatgtag    3540
ttcactcgac aaagactttg tcaagtgtcc gataaaaagt actcgacaaa gaagccgttg    3600
tcgatgtact gttcgtcgag atctcttgt cgagtgtcac actaggcaaa gtctttacgg    3660
agtgtttttc aggctttgac actcggcaaa gcgctcgatt ccagtagtga cagtaatttg    3720
catcaaaaat agctgagaga tttaggcccc gtttcaatct cacgggataa agtttagctt    3780
cctgctaaac tttagctata tgaattgaag tgctaaagtt tagtttcaat taccaccatt    3840
```

```
agctctcctg tttagattac aaatggctaa aagtagctaa aaaatagctg ctaaagttta    3900
tctcgcgaga ttgaaacagg gccttaaaat gagtcaacta atagaccaac taattattag    3960
ctattagtcg ttagcttctt taatctaagc taaaaccaac taatagctta tttgttgaat    4020
tacaattagc tcaacggaat tctctgtttt tctaaaaaaa aactgcccct ctcttacagc    4080
aaattgtccg ctgcccgtcg tccagataca atgaacgtac ctagtaggaa ctctttttaca   4140 cgctcggtcg ctcgccgcgg atcggagtcc ccggaacacg acaccactgt ggaacacgac    4200
aaagtctgct cagaggcggc cacaccctgg cgtgcaccga gccggagccc ggataagcac    4260
ggtaaggaga gtacggcggg acgtggcgac ccgtgtgtct gctgccacgc agccttcctc    4320
cacgtagccg cgcggccgcg ccacgtacca gggcccggcg ctggtataaa tgcgcgccac    4380
ctccgcttta gttctgcata cagccaaccc aaggatccaa cacacacccg aggatatcac    4440
agtcgacact acaccatggg ggagccgcat ccgcacctcg tcctcgacga cctcctcgcg    4500
gggtttgagg cgccctgcgt cgcagacatc aagatcggcg ccatcacgtg gccaccgagt    4560
tcgccggagc cctacatcgc caagtacctc gccaaggacc gcgggaccac gagcgttctg    4620
ctcggattcc gcgtcttgcg tccgagtcgt cggccccgag ggcgccgtgt ggcggacgga    4680
gcgcccggag gtgaaggcta tggacaccgt cggcgtccgc cgcgtgctcc ggcgctacgt    4740
gtcatccgct tgccgacgag gggatggact gcgcgctcgc ggcggcggtg tacgaggaa     4800 aaggtggagt cttgtcacag ctgcgcgagc tcaaggcatg gttggaggag cagactctgt    4860
tccacttcta ctcggcgtcg attcttctgg gctatgatgc tgctgcagat agccttcacc    4920
tccgggcgct ccgtccgcca cacggcgccc tcgggccgga cgactcggac gcaagacgcg    4980
gaatccgagc agaacgctcg tggtcccgcg gtccttggcg aggtacttgg cgatgtaggg    5040
ctccggcgaa ctcggtggcc acgtgatggc gccgatcttg atgtctgcga cgcagggcgc    5100
ctcaaacccc gcgaggaggt cgtcgaggac gaggtgcgga tgcggctcgt taactagcgg    5160
ccgaagcttc ggtccgggtc acccggtccg ggcctagaag gccgatctcc cgggcaccca    5220
gctttcttgt acaaagtggc cgttaacgga tcggccagaa tggcccggac cgggttaccc    5280
ggaccgaagc ttgcatgcct gca                                            5303

<210> SEQ ID NO 12
<211> LENGTH: 7916
<212> TYPE: DNA
<213> ORGANISM: Artificial Sequence
<220> FEATURE:
<223> OTHER INFORMATION: plasmid PHP 21334
<220> FEATURE:
<221> NAME/KEY: promoter
<222> LOCATION: (1)...(875)
<223> OTHER INFORMATION: Ole promoter
<220> FEATURE:
<221> NAME/KEY: misc_RNA
<222> LOCATION: (1006)...(2034)
<223> OTHER INFORMATION: fragment of Zea mays ITPK5 gene
<220> FEATURE:
<221> NAME/KEY: misc_RNA
<222> LOCATION: (2067)...(2494)
<223> OTHER INFORMATION: complement of fragment of Zea mays ITPK5 gene
<220> FEATURE:
<221> NAME/KEY: promoter
<222> LOCATION: (2617)...(4018)
<223> OTHER INFORMATION: Glb1 promoter
<220> FEATURE:
<221> NAME/KEY: misc_RNA
<222> LOCATION: (4060)...(4511)
<223> OTHER INFORMATION: fragment of Zea mays IPPK gene
<220> FEATURE:
```

```
<221> NAME/KEY: misc_RNA
<222> LOCATION: (4513)...(4752)
<223> OTHER INFORMATION: complement of fragment of Zea mays IPPK gene
<220> FEATURE:
<221> NAME/KEY: promoter
<222> LOCATION: (4888)...(6289)
<223> OTHER INFORMATION: Glb1 promoter
<220> FEATURE:
<221> NAME/KEY: 5'UTR
<222> LOCATION: (6334)...(6514)
<223> OTHER INFORMATION: 5' UTR of Zea mays IP2K gene
<220> FEATURE:
<221> NAME/KEY: misc_RNA
<222> LOCATION: (6515)...(7366)
<223> OTHER INFORMATION: first 847 bp of Zea mays IP2K gene
<220> FEATURE:
<221> NAME/KEY: misc_RNA
<222> LOCATION: (7367)...(7798)
<223> OTHER INFORMATION: complement of fragment of Zea mays IP2K gene

<400> SEQUENCE: 12
gatccgattg actatctcat tcctccaaac ccaaacacct caaatatatc tgctatcggg      60
attggcattc ctgtatccct acgcccgtgt acccccctgtt tagagaacct cccaaggtat    120
aagatggcga agattattgt tgtcttgtct ttcatcatat atcgagtctt tccctaggat    180
attattattg gcaatgagca ttacacggtt aatcgattga gagaacatgc atctcacctt    240
cagcaaataa ttacgataat ccatatttta cgcttcgtaa cttctcatga gtttcgatat    300
acaaatttgt tttctggaca ccctaccatt catcctcttc ggagaagaga ggaagtgtcc    360
tcaatttaaa tatgttgtca tgctgtagtt cttcacccaa tctcaacagg taccaagcac    420
attgtttcca caattatat tttagtcaca ataaatctat attattatta atatactaaa    480
actatactga cgctcagatg cttttactag ttcttgctag tatgtgatgt aggtctacgt    540
ggaccagaaa atagtgagac acggaagaca aaagaagtaa aagaggcccg gactacggcc    600
cacatgagat tcggccccgc cacctccggc aaccagcggc cgatccaacg gaagtgcgcg    660
cacacacaca acctcgtata tatcgccgcg cggaagcggc gcgaccgagg aagccttgtc    720
ctcgacaccc cctacacagg tgtcgcgctg ccccgacac gagtcccgca tgcgtcccac    780
gcggccgcgc cagatcccgc ctccgcgcgt tgccacgccc tctataaaca cccagctctc    840
cctcgccctc atctacctca ctcgtagtcg tagctcaagc atcagcggca gcggcagcgg    900
caggagctct gggcagcgtg cgcacgtggg gtacctagct cgctctgcta gcgctaccat    960
gggttatctg cagaattcgc ccttattcct cccgaacccg acccgatggc ctccgacgcc   1020
gccgccgagc cctcctccgg cgtcacccac ccccgcgct acgtcatcgg ttacgcgctc   1080
gcgccgaaga agcagcagag cttcatccag ccgtcgctgg tggcccaggc ggcgtcgcgg   1140
ggcatgacc tcgtccccgt ggatgcgtcg cagcccctgg cagagcaagg gcccttccac   1200
ctcctcatcc acaagctcta cggagacgac tggcgcgccc agctcgtggc cttcgccgcg   1260
cgccacccgg ccgtccccat cgtcgacccg cccctcgcca tcgaccgcct ccacaaccgc   1320
atctccatgc tccaggtcgt ctccgagctc gaccacgccg ccgaccagga cagcactttc   1380
ggtatcccca gccaggtcgt cgtctacgac gctgccgcgc ttgccgactt cggactcctt   1440
gccgcgctcc gcttcccgct catcgccaag cccctcgtcg ccgacggcac cgccaagtcc   1500
cacaagatgt cgctcgtcta ccaccgcgag ggcctcggca agctccgccc gccgcttgtg   1560
ctccaggaat tcgtcaacca tggcggcgtc atcttcaagg tctacgtcgt cggcggccac   1620
gtcacttgcg tcaagcgccg tagcctgccc gacgtgtccc ccgaggatga cgcatcggcc   1680
cagggatccg tctccttctc ccaggtctcc aacctcccca ctgagcgcac ggcggaggag   1740
```

```
tactacggcg aaaagagtct cgaggacgcc gtcgtgccgc ccgccgcatt catcaaccag   1800
atcgcgggcg gcctccgccg cgcgctgggc ctgcaactct tcaacttcga catgatccgc   1860
gacgtccgcg ccggcgaccg ctatctcgtc attgacatca actacttccc gggctacgcc   1920
aagatgccag gatacgagac tgtcctcacg gatttcttct gggagatggt ccataaggac   1980
ggcgtgggca accaacagga ggagaaaggg gccaaccatg ttgtcgtgaa ataagatgat   2040
gattgatggc actggataac agatctccga agtcggcaag cgcggcagcg tcgtagacga   2100
cgacctggct ggggatatccg aaagtgctgt cctggtcggc ggtgtggtcg agctcggaga   2160
cgacctggag catggagatg cggttgtgga ggcggtcgat ggcgaggggc gggtcgacga   2220
tggggacggc cgggtggcgc gcggcgaagg ccacgagctg ggcgcgccag tcgtctccgt   2280
agagcttgtg gatgaggagg tggaagggcc cttgctctgc caggggctgc gacgcatcca   2340
cggggacgag gtccatgccc cgcgacgccc cctgggccac cagcgacggc tggatgaagc   2400
tctgctgctt cttcggcgcg agcgcgtaac cgatgacgta gcgcgggggg tgggtgacgc   2460
cggaggaggg ctcggcggcg gcgtcggagg ccataagctt ggcctagaag gccggtcacc   2520
cggtccgggc ctagaaggcc agcttcaagt ttgtacaaaa aagcaggctc cggccagaat   2580
ggcccggacc gggttacccg gaccggaatt cgattaagct tgccgagtgc atccttgga   2640 cactcgataa agtatatttt atttttttta ttttgccaac caaacttttt gtggtatgtt   2700
cctacactat gtagatctac atgtaccatt ttggcacaat tacatattta caaaatgtt   2760 ttctataaat attagattta gttcgtttat ttgaatttct tcggaaaatt cacatttaaa   2820
ctgcaagtca ctcgaaacat ggaaaaccgt gcatgcaaaa taatgatat gcatgttatc   2880 tagcacaagt tacgaccgat ttcagaagca gaccagaatc ttcaagcacc atgctcacta   2940
aacatgaccg tgaacttgtt atctagttgt ttaaaaattg tataaaacac aaataaagtc   3000
agaaattaat gaaacttgtc cacatgtcat gatatcatat atagaggttg tgataaaaat   3060
ttgataatgt ttcggtaaag ttgtgacgta ctatgtgtag aaacctaagt gacctacaca   3120
taaaatcata gagtttcaat gtagttcact cgacaaagac tttgtcaagt gtccgataaa   3180
aagtactcga caaagaagcc gttgtcgatg tactgttcgt cgagatctct tgtcgagtg   3240 tcacactagg caaagtcttt acggagtgtt tttcaggctt tgacactcgg caaagcgctc   3300
gattccagta gtgacagtaa tttgcatcaa aaatagctga gagatttagg ccccgtttca   3360
atctcacggg ataaagttta gcttcctgct aaactttagc tatatgaatt gaagtgctaa   3420
agtttagttt caattaccac cattagctct cctgtttaga ttacaaatgg ctaaaagtag   3480
ctaaaaaata gctgctaaag tttatctcgc gagattgaaa cagggcctta aaatgagtca   3540
actaatagac caactaatta ttagctatta gtcgttagct tctttaatct aagctaaaac   3600
caactaatag cttatttgtt gaattacaat tagctcaacg gaattctctg ttttctaaa   3660 aaaaaactgc ccctctctta cagcaaattg tccgctgccc gtcgtccaga tacaatgaac   3720
gtacctagta ggaactcttt tacacgctcg gtcgctcgcc gcggatcgga gtccccggaa   3780
cacgacacca ctgtggaaca cgacaaagtc tgctcagagg cggccacacc ctggcgtgca   3840
ccgagccgga gcccggataa gcacggtaag gagagtacgg cgggacgtgg cgacccgtgt   3900
gtctgctgcc acgcagcctt cctccacgta gccgcgcggc cgcgccacgt accagggccc   3960
ggcgctggta taaatgcgcg ccacctccgc tttagttctg catacagcca acccaaggat   4020
ccaacacaca cccgaggata tcacagtcga cactacacca tgggggagcc gcatccgcac   4080
```

```
ctcgtcctcg acgacctcct cgcggggttt gaggcgccct gcgtcgcaga catcaagatc    4140
ggcgccatca cgtggccacc gagttcgccg gagccctaca tcgccaagta cctcgccaag    4200
gaccgcggga ccacgagcgt tctgctcgga ttccgcgtct tgcgtccgag tcgtcggccc    4260
cgagggcgcc gtgtggcgga cggagcgccc ggaggtgaag gctatggaca ccgtcggcgt    4320
ccgccgcgtg ctccggcgct acgtgtcatc cgcttgccga cgaggggatg gactgcgcgc    4380
tcgcggcggc ggtgtacgga ggaaaaggtg gagtcttgtc acagctgcgc gagctcaagg    4440
catggttgga ggagcagact ctgttccact tctactcggc gtcgattctt ctgggctatg    4500
atgctgctgc agatagcctt cacctccggg cgctccgtcc gccacacggc gccctcgggg    4560
ccgacgactc ggacgcaaga cgcggaatcc gagcagaacg ctcgtggtcc cgcggtcctt    4620
ggcgaggtac ttggcgatgt agggctccgg cgaactcggt ggccacgtga tggcgccgat    4680
cttgatgtct gcgacgcagg gcgcctcaaa ccccgcgagg aggtcgtcga ggacgaggtg    4740
cggatgcggc tcgttaacta gcggccgaag cttcggtccg ggtcacccgg tccgggccta    4800
gaaggccgat ctcccgggca cccagctttc ttgtacaaag tggccgttaa cggatcggcc    4860
agaatggccc ggaccggaat tcgattaagc ttgccgagtg ccatccttgg acactcgata    4920
aagtatattt tatttttttt attttgccaa ccaaacttttt tgtggtatgt tcctacacta    4980
tgtagatcta catgtaccat tttggcacaa ttacatattt acaaaaatgt tttctataaa    5040
tattagattt agttcgttta tttgaatttc ttcggaaaat tcacatttaa actgcaagtc    5100
actcgaaaca tggaaaaccg tgcatgcaaa ataaatgata tgcatgttat ctagcacaag    5160
ttacgaccga tttcagaagc agaccagaat cttcaagcac catgctcact aaacatgacc    5220
gtgaacttgt tatctagttg tttaaaaatt gtataaaaca caaataaagt cagaaattaa    5280
tgaaacttgt ccacatgtca tgatatcata tatagaggtt gtgataaaaa tttgataatg    5340
tttcggtaaa gttgtgacgt actatgtgta gaaacctaag tgacctacac ataaaatcat    5400
agagtttcaa tgtagttcac tcgacaaaga ctttgtcaag tgtccgataa aaagtactcg    5460
acaaagaagc cgttgtcgat gtactgttcg tcgagatctc tttgtcgagt gtcacactag    5520
gcaaagtctt tacggagtgt ttttcaggct ttgacactcg gcaaagcgct cgattccagt    5580
agtgacagta atttgcatca aaaatagctg agagatttag gccccgtttc aatctcacgg    5640
gataaagttt agcttcctgc taaactttag ctatatgaat tgaagtgcta aagtttagtt    5700
tcaattacca ccattagctc tcctgtttag attacaaatg gctaaaagta gctaaaaaat    5760
agctgctaaa gtttatctcg cgagattgaa acagggcctt aaaatgagtc aactaataga    5820
ccaactaatt attagctatt agtcgttagc ttctttaatc taagctaaaa ccaactaata    5880
gcttatttgt tgaattacaa ttagctcaac ggaattctct gtttttctaa aaaaaaactg    5940
cccctctctt acagcaaatt gtccgctgcc cgtcgtccag atacaatgaa cgtacctagt    6000
aggaactctt ttacacgctc ggtcgctcgc gcggatcgg agtccccgga acacgacacc    6060
actgtggaac acgacaaagt ctgctcagag gcggccacac cctggcgtgc accgagccgg    6120
agcccggata agcacggtaa ggagagtacg gcggacgtg gcgacccgtg tgtctgctgc    6180
cacgcagcct tcctccacgt agccgcgcgg ccgcgccacg taccagggcc ggcgctggt    6240
ataaatgcgc gccacctccg ctttagttct gcatacagcc aacccaagga tccaacacac    6300
acccgaggat atcacagtcg acccacgcgt ccgagcacca gcatctcttc aggtctccac    6360
caagcgcaga caccgcagca gcggcagcgg cacgatctgg tgaccccccc gccgcgtcaa    6420
gcctgctcct ccggtgatcg ccggactggc ggggtaggaa ccagcggagc gcagcccgcc    6480
```

-continued

```
tccttccgct gtgtctgaca gcagcagatc ctcgatggag atggatgggg ttctgcaagc    6540
cgcggatgcc aaggattggg tttacaaggg ggaaggcgcc gcgaatctta tcctcagcta    6600
caccggctcg tcgccctcca tgcttggcaa ggtactgcgg ctcaagaaga ttctaaaaaa    6660
caagtcgcag cggcaccaa gttgtattgt attctcaagt catgagcaac tcctgtgggg    6720
ccatatccca gaactggttg agtcggtcaa acaagattgc ttggctcaag cctatgcagt    6780
gcatgttatg agccaacacc tgggtgccaa tcatgtcgat ggtggggtcc gtgtacgtgt    6840
ttctagggat tttctggagc ttgtcgaaaa gaatgttctt agcagccgtc ctgctgggag    6900
agtaaatgca agttcaattg ataacactgc tgatgccgct cttctgatag cagaccactc    6960
tttattttct ggcaatccta agggtagcag ctgcatagct gtagagataa aggccaaatg    7020
tgggtttctg ccatcatcag aatatatatc agaagataat actatcaaga aacaagtaac    7080
gagatataag atgcatcagc acctcaaatt ttatcagggt gagatatcga agactagtga    7140
gtacaatcct cttgatctat tttctgggtc aaaagagaga atatgcatgg ccatcaagtc    7200
ccttttctca actcctcaga caacttaag gattttgtc aatggatctt tagcttttgg     7260
tggcatggga ggtggtgcag atagtgttca tcctgctgac actcttaagt gtcttgaaga    7320
tctcagcaag attagtggcc taaaactccc tgacttcact gagctctcgt tacttgtttc    7380
ttgatagtat tatcttctga tatatattct gatgatggca gaaacccaca tttggccttt    7440
atctctacag ctatgcagct gctacccta ggattgccag aaaataaaga gtggtctgct     7500
atcagaagag cggcatcagc agtgttatca attgaacttg catttactct cccagcagga    7560
cggctgctaa gaacattctt ttcgacaagc tccagaaaat ccctagaaac acgtacacgg    7620
accccaccat cgacatgatt ggcacccagg tgttggctca taacatgcac tgcataggct    7680
tgagccaagc aatcttgttt gaccgactca accagttctg ggatatggcc cacaggagt     7740
tgctcatgac ttgagaatac aatacaactt ggtgcccgct cgacttgtt ttttagaaag     7800
cttcggtccg ggcctagaag gccagcttgc ggccgccccg ggcaacttta ttatacaaag    7860
ttgatagata tcggaccgat taaactttaa ttcggtccga agcttgcatg cctgca        7916
```

<210> SEQ ID NO 13
<211> LENGTH: 1170
<212> TYPE: DNA
<213> ORGANISM: Zea mays
<220> FEATURE:
<221> NAME/KEY: source
<222> LOCATION: (0)...(0)
<223> OTHER INFORMATION: Zea mays IPPK cDNA

<400> SEQUENCE: 13

```
gaaaatctct ttctccgctg cgctgcaaac ccaccgcttc caccatcgcc actcgtcacc      60
ccttgctccc atagtcccca taccatgccc gacctccacc cgccgagca ccaagtcgcc     120
ggtcaccgcg cctccgccag caagctgggc ccgctcatcg acggctccgg cctcttctac     180
aagccgctcc aggccggcga ccgtggggag cacgaggtcg ccttctatga ggcgttctcc     240
gcccacgccg ccgtcccggc cgcatccga dacaccttct tcccccggtt ccacggcacg     300
cgactcctcc ccaccgaggc gcagcccggg gagccgcatc cgcacctcgt cctcgacgac     360
ctcctcgcgg ggtttgaggc gccctgcgtc gcagacatca agatcggcgc catcacgtgg     420
ccaccgagtt cgccggagcc ctacatcgcc aagtacctcg ccaaggaccg cgggaccacg    480
agcgttctgc tcggattccg cgtcttgcgt ccgagtcgtc ggccccgagg gcgccgtgtg    540
```

| | |
|---|---|
| gcggacggag cgcccggagg tgaaggctat ggacaccgtc ggcgtccgcc gcgtgctccg | 600 |
| gcgctacgtg tcatccgctt gccgacgagg ggatggactg cgcgctcgcg cggcggtgt | 660 |
| acggaggaaa aggtggagtc ttgtcacagc tgcgcgagct caaggcatgg ttggaggagc | 720 |
| agactctgtt ccacttctac tcggcgtcga ttcttctggg ctatgatgct gctgcagtcg | 780 |
| cagcaggcgg aggtggggt gggtaacag tgaagctggt ggactttgcc catgtgcccg | 840 |
| agggtgatgg ggtgattgac cacaacttcc tgggcgagct ctgctagctg atcaagttcg | 900 |
| tttctgacat tgttccagag actccttaga cgcagccttt gggtccttct taagagagga | 960 |
| tcctgacatt tttgatttga taacaaagga agcactttca gctgcaaaaa agaaagcag | 1020 |
| cagtgaggat gaagatgaca gtagtgagga aagttcggat gatgagccaa caaaagttga | 1080 |
| agaaaagaag gctccaaaag tatcagaaaa cattggatct gaggatgaat cttctgaaga | 1140 |
| cgagagtgat aaagacagtg aagagcctca | 1170 |

<210> SEQ ID NO 14
<211> LENGTH: 1400
<212> TYPE: DNA
<213> ORGANISM: Zea mays
<220> FEATURE:
<221> NAME/KEY: source
<222> LOCATION: (0)...(0)
<223> OTHER INFORMATION: Zea mays ITPK5 cDNA

<400> SEQUENCE: 14

| | |
|---|---|
| ccacgcgtcc gcaaatttca atctccatcg atcgattcct cccgaacccg acccgatggc | 60 |
| ctccgacgcc gccgccgagc cctcctccgg cgtcacccac ccccgcgct acgtcatcgg | 120 |
| ttacgcgctc gcgccgaaga agcagcaaag cttcatccag ccgtcgctgg tggcccaggc | 180 |
| ggcgtcgcgg ggcatggacc tcgtccccgt ggatgcgtcg cagcccctgg cagagcaagg | 240 |
| gcccttccac ctcctcatcc acaagctcta cggagacgac tggcgcgccc agctcgtggc | 300 |
| cttcgccgcg cgccacccgg ccgtccccat cgtcgacccg cccacgcca tcgaccgcct | 360 |
| ccacaaccgc atctccatgc tccaggtcgt ctccgagctc gaccacgccg ccgaccagga | 420 |
| cagcactttc ggtatcccca gccaggtcgt cgtctacgac gctgccgcgc tcgccgactt | 480 |
| cggactcctt gccgcgctcc gcttcccgct catcgccaag ccctcgtcg ccgacggcac | 540 |
| cgccaagtcc cacaagatgt cgctcgtcta ccaccgcgag ggcctcggca agctccgccc | 600 |
| gccgcttgtg ctccaggagt tcgtcaacca tggcggcgtc atcttcaagg tctacgtcgt | 660 |
| cggcggccac gtcacttgcg tcaagcgccg tagcctgccc gacgtgtccc ccgaggatga | 720 |
| cgcatcggcc cagggatccg tctccttctc ccaggtctcc aacctcccca ctgagcgcac | 780 |
| ggcggaggag tactacggcg aaaagagtct cgaggacgcc gtcgtgccgc ccgccgcatt | 840 |
| catcaaccag atcgcgggcg gcctccgccg cgcgctgggc ctgcaactct tcaacttcga | 900 |
| catgatccgc gacgtccgcg ccggcgaccg ctatctcgtc attgacatca actacttccc | 960 |
| gggctacgcc aagatgccag gatacgagac tgtcctcacg gatttcttct gggagatggt | 1020 |
| ccataaggac ggcgtgggca accaacagga ggagaaaggg gccaaccatg ttgtcgtgaa | 1080 |
| ataagatgat gattgatggc actggatatc tggcgaatgc tgctgattct ggatgcagaa | 1140 |
| ttcgatgagg ggatttagtt ggttgtagta tctggcgaat gctgctggtt ctggatgcag | 1200 |
| aatttgatga ggggatttag ttggatttca acccatagca tgccgaggac ctcctagctc | 1260 |
| tttccaaacc agttgtttag gtatcttttc tgggtaagtc agcttcatct agtttagtct | 1320 |
| gtctgaacaa aagagtggga catgacccaa acggaattct aatgaaaaac gagctctcta | 1380 |

```
tctgcaaaaa aaaaaaaaaa                                              1400

<210> SEQ ID NO 15
<211> LENGTH: 1936
<212> TYPE: DNA
<213> ORGANISM: Zea mays
<220> FEATURE:
<221> NAME/KEY: source
<222> LOCATION: (0)...(0)
<223> OTHER INFORMATION: Zea mays IP2K-1 cDNA
<220> FEATURE:
<221> NAME/KEY: CDS
<222> LOCATION: (199)...(1521)

<400> SEQUENCE: 15
gtcgacccac gcgtccgagc accagcatct cttcaggtct ccaccaagcg cagacaccgc    60
agcagcggca gcggcacgat ctggtgaccc ccccgccgcg tcaagcctgc tcctccggtg   120
atcgccggac tggcggggta ggaaccagcg gagcgcagcc cgcctccttc cgctgtgtct   180
gacagcagca gatcctcg atg gag atg gat ggg gtt ctg caa gcc gcg gat    231
                   Met Glu Met Asp Gly Val Leu Gln Ala Ala Asp
                    1               5                  10 gcc aag gat tgg gtt tac aag ggg gaa ggc gcc gcg aat ctt atc ctc    279
Ala Lys Asp Trp Val Tyr Lys Gly Glu Gly Ala Ala Asn Leu Ile Leu
            15                  20                  25 agc tac acc ggc tcg tcg ccc tcc atg ctt ggc aag gta ctg cgg ctc    327
Ser Tyr Thr Gly Ser Ser Pro Ser Met Leu Gly Lys Val Leu Arg Leu
        30                  35                  40 aag aag att cta aaa aac aag tcg cag cgg gca cca agt tgt att gta    375
Lys Lys Ile Leu Lys Asn Lys Ser Gln Arg Ala Pro Ser Cys Ile Val
    45                  50                  55 ttc tca agt cat gag caa ctc ctg tgg ggc cat atc cca gaa ctg gtt    423
Phe Ser Ser His Glu Gln Leu Leu Trp Gly His Ile Pro Glu Leu Val
60                  65                  70                  75 gag tcg gtc aaa caa gat tgc ttg gct caa gcc tat gca gtg cat gtt    471
Glu Ser Val Lys Gln Asp Cys Leu Ala Gln Ala Tyr Ala Val His Val
                80                  85                  90 atg agc caa cac ctg ggt gcc aat cat gtc gat ggt ggg gtc cgt gta    519
Met Ser Gln His Leu Gly Ala Asn His Val Asp Gly Gly Val Arg Val
            95                 100                 105 cgt gtt tct agg gat ttt ctg gag ctt gtc gaa aag aat gtt ctt agc    567
Arg Val Ser Arg Asp Phe Leu Glu Leu Val Glu Lys Asn Val Leu Ser
       110                 115                 120 agc cgt cct gct ggg aga gta aat gca agt tca att gat aac act gct    615
Ser Arg Pro Ala Gly Arg Val Asn Ala Ser Ser Ile Asp Asn Thr Ala
   125                 130                 135 gat gcc gct ctt ctg ata gca gac cac tct tta ttt tct ggc aat cct    663
Asp Ala Ala Leu Leu Ile Ala Asp His Ser Leu Phe Ser Gly Asn Pro
140                 145                 150                 155 aag ggt agc agc tgc ata gct gta gag ata aag gcc aaa tgt ggg ttt    711
Lys Gly Ser Ser Cys Ile Ala Val Glu Ile Lys Ala Lys Cys Gly Phe
                160                 165                 170 ctg cca tca tca gaa tat ata tca gaa gat aat act atc aag aaa caa    759
Leu Pro Ser Ser Glu Tyr Ile Ser Glu Asp Asn Thr Ile Lys Lys Gln
            175                 180                 185 gta acg aga tat aag atg cat cag cac ctc aaa ttt tat cag ggt gag    807
Val Thr Arg Tyr Lys Met His Gln His Leu Lys Phe Tyr Gln Gly Glu
        190                 195                 200 ata tcg aag act agt gag tac aat cct ctt gat cta ttt tct ggg tca    855
Ile Ser Lys Thr Ser Glu Tyr Asn Pro Leu Asp Leu Phe Ser Gly Ser
    205                 210                 215
```

```
aaa gag aga ata tgc atg gcc atc aag tcc ctt ttc tca act cct cag    903
Lys Glu Arg Ile Cys Met Ala Ile Lys Ser Leu Phe Ser Thr Pro Gln
220                 225                 230                 235 aac aac tta agg att ttt gtc aat gga tct tta gct ttt ggt ggc atg    951
Asn Asn Leu Arg Ile Phe Val Asn Gly Ser Leu Ala Phe Gly Gly Met
                240                 245                 250 gga ggt ggt gca gat agt gtt cat cct gct gac act ctt aag tgt ctt    999
Gly Gly Gly Ala Asp Ser Val His Pro Ala Asp Thr Leu Lys Cys Leu
            255                 260                 265 gaa gat ctc agc aag att agt ggc cta aaa ctc cct gac ttc act gag   1047
Glu Asp Leu Ser Lys Ile Ser Gly Leu Lys Leu Pro Asp Phe Thr Glu
        270                 275                 280 ctc ctg tca gag aca att ttt agg tct gag gta tta ggc aac ctg ttg   1095
Leu Leu Ser Glu Thr Ile Phe Arg Ser Glu Val Leu Gly Asn Leu Leu
    285                 290                 295 gcc act caa aag ttg gat gat cat gac att gaa ggg gta att cat ctg   1143
Ala Thr Gln Lys Leu Asp Asp His Asp Ile Glu Gly Val Ile His Leu
300                 305                 310                 315 tac tac aac ata att tct cag cct tgt tta gtc tgc aaa aac cta act   1191
Tyr Tyr Asn Ile Ile Ser Gln Pro Cys Leu Val Cys Lys Asn Leu Thr
                320                 325                 330 gat gta gag cta ttg cgg aag tac act ttc ttg cat tct ctt ccg ttg   1239
Asp Val Glu Leu Leu Arg Lys Tyr Thr Phe Leu His Ser Leu Pro Leu
            335                 340                 345 gac aaa agc ctg aag atc gtt agg gac ttc ctc att tct gct acc gca   1287
Asp Lys Ser Leu Lys Ile Val Arg Asp Phe Leu Ile Ser Ala Thr Ala
        350                 355                 360 aag gac tgt agc ctg atg atc agc ttt cgg cca aga gag aat ggt agt   1335
Lys Asp Cys Ser Leu Met Ile Ser Phe Arg Pro Arg Glu Asn Gly Ser
    365                 370                 375 aca gat tct gag tat gat tca gtg ttt ctt gaa tca gtg aag cga acc   1383
Thr Asp Ser Glu Tyr Asp Ser Val Phe Leu Glu Ser Val Lys Arg Thr
380                 385                 390                 395 tat gag tac aag gca tat ttc ctt gat ctg gat gtg aaa cct ctg gat   1431
Tyr Glu Tyr Lys Ala Tyr Phe Leu Asp Leu Asp Val Lys Pro Leu Asp
                400                 405                 410 aag atg gag cat tat ttt aaa ctg gat cag agg ata gtc aat ttc tac   1479
Lys Met Glu His Tyr Phe Lys Leu Asp Gln Arg Ile Val Asn Phe Tyr
            415                 420                 425 aca aga aat ggg gga ggt ctt gcc atc tcc aaa ggg cag taa            1521
Thr Arg Asn Gly Gly Gly Leu Ala Ile Ser Lys Gly Gln *
        430                 435                 440 taccaaagac acttcgagga tttatacatc tggagaaggg tgcatcaggg agtgttggtt  1581
gttgttcctg ctgcttggtg ctgctgttgt aacttcatga gtacagtccc aaggttggga  1641
ggctcgaccc ttaacgcctg gaaagggcac agggagctgt gttgtccgtc agtcgctgtt  1701
gtaactcaaa ctagtgcata caccgtggct tgtcacggta atttccgaag atgtccaacg  1761
ttagttgaga caaccgaact gcttaccgtg gcaatcactc attgtaacat caagttgaaa  1821
atgagggctg aagtttccct cacaggctac catatgtcag atatgtcctt tgtaccacta  1881
ataagtgccc ctggggtcat gtatgaatgt atctcaattt gctattgcaa aaaaa       1936

<210> SEQ ID NO 16
<211> LENGTH: 440
<212> TYPE: PRT
<213> ORGANISM: Zea mays

<400> SEQUENCE: 16
```

-continued

```
Met Glu Met Asp Gly Val Leu Gln Ala Ala Asp Ala Lys Asp Trp Val
 1               5                  10                  15

Tyr Lys Gly Glu Gly Ala Ala Asn Leu Ile Leu Ser Tyr Thr Gly Ser
                20                  25                  30

Ser Pro Ser Met Leu Gly Lys Val Leu Arg Leu Lys Lys Ile Leu Lys
            35                  40                  45

Asn Lys Ser Gln Arg Ala Pro Ser Cys Ile Val Phe Ser Ser His Glu
 50                  55                  60

Gln Leu Leu Trp Gly His Ile Pro Glu Leu Val Glu Ser Val Lys Gln
 65                  70                  75                  80

Asp Cys Leu Ala Gln Ala Tyr Ala Val His Val Met Ser Gln His Leu
                85                  90                  95

Gly Ala Asn His Val Asp Gly Val Arg Val Arg Val Ser Arg Asp
                100                 105                 110

Phe Leu Glu Leu Val Glu Lys Asn Val Leu Ser Ser Arg Pro Ala Gly
            115                 120                 125

Arg Val Asn Ala Ser Ser Ile Asp Asn Thr Ala Asp Ala Ala Leu Leu
        130                 135                 140

Ile Ala Asp His Ser Leu Phe Ser Gly Asn Pro Lys Gly Ser Ser Cys
145                 150                 155                 160

Ile Ala Val Glu Ile Lys Ala Lys Cys Gly Phe Leu Pro Ser Ser Glu
                165                 170                 175

Tyr Ile Ser Glu Asp Asn Thr Ile Lys Lys Gln Val Thr Arg Tyr Lys
            180                 185                 190

Met His Gln His Leu Lys Phe Tyr Gln Gly Glu Ile Ser Lys Thr Ser
        195                 200                 205

Glu Tyr Asn Pro Leu Asp Leu Phe Ser Gly Ser Lys Glu Arg Ile Cys
    210                 215                 220

Met Ala Ile Lys Ser Leu Phe Ser Thr Pro Gln Asn Asn Leu Arg Ile
225                 230                 235                 240

Phe Val Asn Gly Ser Leu Ala Phe Gly Gly Met Gly Gly Gly Ala Asp
                245                 250                 255

Ser Val His Pro Ala Asp Thr Leu Lys Cys Leu Glu Asp Leu Ser Lys
            260                 265                 270

Ile Ser Gly Leu Lys Leu Pro Asp Phe Thr Glu Leu Leu Ser Glu Thr
        275                 280                 285

Ile Phe Arg Ser Glu Val Leu Gly Asn Leu Leu Ala Thr Gln Lys Leu
    290                 295                 300

Asp Asp His Asp Ile Glu Gly Val Ile His Leu Tyr Tyr Asn Ile Ile
305                 310                 315                 320

Ser Gln Pro Cys Leu Val Cys Lys Asn Leu Thr Asp Val Glu Leu Leu
                325                 330                 335

Arg Lys Tyr Thr Phe Leu His Ser Leu Pro Leu Asp Lys Ser Leu Lys
            340                 345                 350

Ile Val Arg Asp Phe Leu Ile Ser Ala Thr Ala Lys Asp Cys Ser Leu
        355                 360                 365

Met Ile Ser Phe Arg Pro Arg Glu Asn Gly Ser Thr Asp Ser Glu Tyr
    370                 375                 380

Asp Ser Val Phe Leu Glu Ser Val Lys Arg Thr Tyr Glu Tyr Lys Ala
385                 390                 395                 400

Tyr Phe Leu Asp Leu Asp Val Lys Pro Leu Asp Lys Met Glu His Tyr
                405                 410                 415

Phe Lys Leu Asp Gln Arg Ile Val Asn Phe Tyr Thr Arg Asn Gly Gly
```

```
                    420                 425                 430
Gly Leu Ala Ile Ser Lys Gly Gln
        435                 440

<210> SEQ ID NO 17
<211> LENGTH: 1856
<212> TYPE: DNA
<213> ORGANISM: Zea mays
<220> FEATURE:
<221> NAME/KEY: source
<222> LOCATION: (0)...(0)
<223> OTHER INFORMATION: Zea mays IP2K-2 cDNA
<220> FEATURE:
<221> NAME/KEY: CDS
<222> LOCATION: (348)...(1670)

<400> SEQUENCE: 17
gaattcggca cgaggcggct tcgcctgatc gcgtacgccg cttcgtcctg attctcaatc       60
tctggtgctc ccatgaagaa agacagggaa tgaaggaccg ccacctcgcg ctgaaccaga      120
cccagagggt ccgcctcgag gccgcgcttc aagagctcca gtccgttgcg cccgccgctg      180
ccgtcaccgt cgcggacacc attcccgtca atcaaggaga caacatcctc aagggggcatg      240 ggacgtcgga ccaggacggg gaggtggttg cgacgctctg cggggtggtg gagcgggtca      300
acaagctggt ctacgtccgc actcttcgcg cgagctgcag attctcg atg gag atg        356
                                                    Met Glu Met
                                                      1 aat ggg gtt ctg caa gcc gcg gat gcc aag tac tgg gtt tac aag ggt        404
Asn Gly Val Leu Gln Ala Ala Asp Ala Lys Tyr Trp Val Tyr Lys Gly
  5                  10                  15 gag ggc gcc gcg aat ctc atc ctc agc tac acc ggc tca tcc cct act        452
Glu Gly Ala Ala Asn Leu Ile Leu Ser Tyr Thr Gly Ser Ser Pro Thr
 20                  25                  30                  35 atg ctt ggc aag gta ttg cgg gtc aag aag ctt cta aat gac aag tca        500
Met Leu Gly Lys Val Leu Arg Val Lys Lys Leu Leu Asn Asp Lys Ser
                 40                  45                  50 cag ctg cca cca agt tgt atg gtc ttc tca agt cat gag caa ctc ctg        548
Gln Leu Pro Pro Ser Cys Met Val Phe Ser Ser His Glu Gln Leu Leu
             55                  60                  65 tgg ggc cat att cca gaa ctg gtt gag tct gtc aaa caa gat tgc ttg        596
Trp Gly His Ile Pro Glu Leu Val Glu Ser Val Lys Gln Asp Cys Leu
         70                  75                  80 gct caa gcc tat gct gta cat gtt atg agc caa cat ctg ggt gcc aat        644
Ala Gln Ala Tyr Ala Val His Val Met Ser Gln His Leu Gly Ala Asn
     85                  90                  95 cat gtc gat ggt ggg gtt cat gta cgt gtt tct agg gat ttt cta gag        692
His Val Asp Gly Gly Val His Val Arg Val Ser Arg Asp Phe Leu Glu
100                 105                 110                 115 ctt gtt gaa aag aat gtt ctt agc agc cgt cct cct tgg aga gta aat        740
Leu Val Glu Lys Asn Val Leu Ser Ser Arg Pro Pro Trp Arg Val Asn
                120                 125                 130 gca agt tca att gat atc act gct gat gcc gct ctt cta ata gca gac        788
Ala Ser Ser Ile Asp Ile Thr Ala Asp Ala Ala Leu Leu Ile Ala Asp
            135                 140                 145 cac tct tta ttc tct ggt act cca aag ggt agc agc tgc ata gct gta        836
His Ser Leu Phe Ser Gly Thr Pro Lys Gly Ser Ser Cys Ile Ala Val
        150                 155                 160 gag ata aag gcc aaa tgt ggg ttt gtg cca tca tca gaa tat ata tca        884
Glu Ile Lys Ala Lys Cys Gly Phe Val Pro Ser Ser Glu Tyr Ile Ser
    165                 170                 175 aaa gat aat tct atc aag aaa caa gta acg aga tat aaa atg cat cag        932
```

```
Lys Asp Asn Ser Ile Lys Lys Gln Val Thr Arg Tyr Lys Met His Gln
180                 185                 190                 195 cac ctc aaa ttt cat cag ggt gag ata tcg aag act agt gaa tac aat        980
His Leu Lys Phe His Gln Gly Glu Ile Ser Lys Thr Ser Glu Tyr Asn
                200                 205                 210 cct ctt gat cta ttt tct gag tcg aaa gaa aga ata agc atg gcc atc       1028
Pro Leu Asp Leu Phe Ser Glu Ser Lys Glu Arg Ile Ser Met Ala Ile
                215                 220                 225 aag tca ttt ttc tca act cct cag aac aac ttc agg att ttt gtc aat       1076
Lys Ser Phe Phe Ser Thr Pro Gln Asn Asn Phe Arg Ile Phe Val Asn
            230                 235                 240 gga tct tta gct ttt ggt ggc atg gga ggt ggt gca gat agt gtt cat       1124
Gly Ser Leu Ala Phe Gly Gly Met Gly Gly Gly Ala Asp Ser Val His
        245                 250                 255 cct gct gac act gat aag tgc att aaa gat ctc agc aag gtc agt ggc       1172
Pro Ala Asp Thr Asp Lys Cys Ile Lys Asp Leu Ser Lys Val Ser Gly
260                 265                 270                 275 ctg gaa ctc cct gac ttc act gag ctc ctg tca gag aca att ttc aaa       1220
Leu Glu Leu Pro Asp Phe Thr Glu Leu Leu Ser Glu Thr Ile Phe Lys
                280                 285                 290 tct ggg gta ttg ggc aaa ctg ttg acc act caa aag ctg gat gat cat       1268
Ser Gly Val Leu Gly Lys Leu Leu Thr Thr Gln Lys Leu Asp Asp His
                295                 300                 305 gac att gaa ggg gca att cat ctg tac tac aac ata att tct cag cct       1316
Asp Ile Glu Gly Ala Ile His Leu Tyr Tyr Asn Ile Ile Ser Gln Pro
            310                 315                 320 tgt tta gtc tgc aaa aac cta act gat gta gag cta ttg cgg aag tac       1364
Cys Leu Val Cys Lys Asn Leu Thr Asp Val Glu Leu Leu Arg Lys Tyr
        325                 330                 335 aca ctc ttg cat tct ctt ccg ttg gac aag agc ttg aag att gtc aga       1412
Thr Leu Leu His Ser Leu Pro Leu Asp Lys Ser Leu Lys Ile Val Arg
340                 345                 350                 355 aac ttc ctc att tct gct act gca aag gac tgt agc ctg atg atc agc       1460
Asn Phe Leu Ile Ser Ala Thr Ala Lys Asp Cys Ser Leu Met Ile Ser
                360                 365                 370 ttt cgg cca aga gag aat gga agt aca gat tct gag tat gat tca gtg       1508
Phe Arg Pro Arg Glu Asn Gly Ser Thr Asp Ser Glu Tyr Asp Ser Val
                375                 380                 385 ttt ctt gaa tca gcg aag cga acc tat gag tac aag aca tat ttc gtt       1556
Phe Leu Glu Ser Ala Lys Arg Thr Tyr Glu Tyr Lys Thr Tyr Phe Val
            390                 395                 400 gat ctg gat gtg aaa cct ctg gac aag atg gta cat tat ttt aaa ctg       1604
Asp Leu Asp Val Lys Pro Leu Asp Lys Met Val His Tyr Phe Lys Leu
        405                 410                 415 gat cag agg ata gtc aat tcc tac aca aga tat ggg gag gtc ttg cca       1652
Asp Gln Arg Ile Val Asn Ser Tyr Thr Arg Tyr Gly Glu Val Leu Pro
420                 425                 430                 435 cct cca aag ggc aag taa taccaaagac acttcggcga ttcagctcca              1700
Pro Pro Lys Gly Lys *
                440 acaatgagga gcctctcttc ttactatata cgtctggact atggagaagg gtgcatcaga     1760 gagctccagc ccactacgcc cttaggttct gtgcatatat tgttgtatct cttaactgtt     1820 tgatgatatg gaatatcttt tcccaatatg gtaccg                               1856

<210> SEQ ID NO 18
<211> LENGTH: 440
<212> TYPE: PRT
<213> ORGANISM: Zea mays
```

<400> SEQUENCE: 18

```
Met Glu Met Asn Gly Val Leu Gln Ala Ala Asp Ala Lys Tyr Trp Val
 1               5                  10                  15

Tyr Lys Gly Glu Gly Ala Ala Asn Leu Ile Leu Ser Tyr Thr Gly Ser
                20                  25                  30

Ser Pro Thr Met Leu Gly Lys Val Leu Arg Val Lys Lys Leu Leu Asn
            35                  40                  45

Asp Lys Ser Gln Leu Pro Pro Ser Cys Met Val Phe Ser Ser His Glu
        50                  55                  60

Gln Leu Leu Trp Gly His Ile Pro Glu Leu Val Glu Ser Val Lys Gln
65                  70                  75                  80

Asp Cys Leu Ala Gln Ala Tyr Ala Val His Val Met Ser Gln His Leu
                85                  90                  95

Gly Ala Asn His Val Asp Gly Val His Val Arg Val Ser Arg Asp
                100                 105                 110

Phe Leu Glu Leu Val Glu Lys Asn Val Leu Ser Ser Arg Pro Pro Trp
                115                 120                 125

Arg Val Asn Ala Ser Ser Ile Asp Ile Thr Ala Asp Ala Ala Leu Leu
    130                 135                 140

Ile Ala Asp His Ser Leu Phe Ser Gly Thr Pro Lys Gly Ser Ser Cys
145                 150                 155                 160

Ile Ala Val Glu Ile Lys Ala Lys Cys Gly Phe Val Pro Ser Ser Glu
                165                 170                 175

Tyr Ile Ser Lys Asp Asn Ser Ile Lys Lys Gln Val Thr Arg Tyr Lys
                180                 185                 190

Met His Gln His Leu Lys Phe His Gln Gly Glu Ile Ser Lys Thr Ser
            195                 200                 205

Glu Tyr Asn Pro Leu Asp Leu Phe Ser Glu Ser Lys Glu Arg Ile Ser
        210                 215                 220

Met Ala Ile Lys Ser Phe Phe Ser Thr Pro Gln Asn Asn Phe Arg Ile
225                 230                 235                 240

Phe Val Asn Gly Ser Leu Ala Phe Gly Gly Met Gly Gly Gly Ala Asp
                245                 250                 255

Ser Val His Pro Ala Asp Thr Asp Lys Cys Ile Lys Asp Leu Ser Lys
                260                 265                 270

Val Ser Gly Leu Glu Leu Pro Asp Phe Thr Glu Leu Leu Ser Glu Thr
            275                 280                 285

Ile Phe Lys Ser Gly Val Leu Gly Lys Leu Leu Thr Thr Gln Lys Leu
        290                 295                 300

Asp Asp His Asp Ile Glu Gly Ala Ile His Leu Tyr Tyr Asn Ile Ile
305                 310                 315                 320

Ser Gln Pro Cys Leu Val Cys Lys Asn Leu Thr Asp Val Glu Leu Leu
                325                 330                 335

Arg Lys Tyr Thr Leu Leu His Ser Leu Pro Leu Asp Lys Ser Leu Lys
                340                 345                 350

Ile Val Arg Asn Phe Leu Ile Ser Ala Thr Ala Lys Asp Cys Ser Leu
            355                 360                 365

Met Ile Ser Phe Arg Pro Arg Glu Asn Gly Ser Thr Asp Ser Glu Tyr
        370                 375                 380

Asp Ser Val Phe Leu Glu Ser Ala Lys Arg Thr Tyr Glu Tyr Lys Thr
385                 390                 395                 400

Tyr Phe Val Asp Leu Asp Val Lys Pro Leu Asp Lys Met Val His Tyr
                405                 410                 415
```

Phe Lys Leu Asp Gln Arg Ile Val Asn Ser Tyr Thr Arg Tyr Gly Glu
            420                 425                 430

Val Leu Pro Pro Lys Gly Lys
        435             440

<210> SEQ ID NO 19
<211> LENGTH: 526
<212> TYPE: PRT
<213> ORGANISM: zea mays

<400> SEQUENCE: 19

Met Lys Asp Arg His Leu Ala Leu Asn Gln Thr Gln Arg Val Arg Leu
 1               5                  10                  15

Glu Ala Ala Leu Gln Glu Leu Gln Ser Val Ala Pro Ala Ala Ala Val
            20                  25                  30

Thr Val Ala Asp Thr Ile Pro Val Asn Gln Glu Asp Asn Ile Leu Lys
        35                  40                  45

Gly His Gly Thr Ser Asp Gln Asp Gly Glu Val Val Ala Thr Leu Cys
    50                  55                  60

Gly Val Val Glu Arg Val Asn Lys Leu Val Tyr Val Arg Thr Leu Arg
65                  70                  75                  80

Ala Ser Cys Arg Phe Ser Met Glu Met Asn Gly Val Leu Gln Ala Ala
                85                  90                  95

Asp Ala Lys Tyr Trp Val Tyr Lys Gly Glu Gly Ala Ala Asn Leu Ile
            100                 105                 110

Leu Ser Tyr Thr Gly Ser Ser Pro Thr Met Leu Gly Lys Val Leu Arg
        115                 120                 125

Val Lys Lys Leu Leu Asn Asp Lys Ser Gln Leu Pro Pro Ser Cys Met
    130                 135                 140

Val Phe Ser Ser His Glu Gln Leu Leu Trp Gly His Ile Pro Glu Leu
145                 150                 155                 160

Val Glu Ser Val Lys Gln Asp Cys Leu Ala Gln Ala Tyr Ala Val His
                165                 170                 175

Val Met Ser Gln His Leu Gly Ala Asn His Val Asp Gly Gly Val His
            180                 185                 190

Val Arg Val Ser Arg Asp Phe Leu Glu Leu Val Glu Lys Asn Val Leu
        195                 200                 205

Ser Ser Arg Pro Pro Trp Arg Val Asn Ala Ser Ser Ile Asp Ile Thr
    210                 215                 220

Ala Asp Ala Ala Leu Leu Ile Ala Asp His Ser Leu Phe Ser Gly Thr
225                 230                 235                 240

Pro Lys Gly Ser Ser Cys Ile Ala Val Glu Ile Lys Ala Lys Cys Gly
                245                 250                 255

Phe Val Pro Ser Ser Glu Tyr Ile Ser Lys Asp Asn Ser Ile Lys Lys
            260                 265                 270

Gln Val Thr Arg Tyr Lys Met His Gln His Leu Lys Phe His Gln Gly
        275                 280                 285

Glu Ile Ser Lys Thr Ser Glu Tyr Asn Pro Leu Asp Leu Phe Ser Glu
    290                 295                 300

Ser Lys Glu Arg Ile Ser Met Ala Ile Lys Ser Phe Ser Thr Pro
305                 310                 315                 320

Gln Asn Asn Phe Arg Ile Phe Val Asn Gly Ser Leu Ala Phe Gly Gly
                325                 330                 335

Met Gly Gly Gly Ala Asp Ser Val His Pro Ala Asp Thr Asp Lys Cys

-continued

```
                    340             345             350
Ile Lys Asp Leu Ser Lys Val Ser Gly Leu Glu Leu Pro Asp Phe Thr
        355                 360                 365
Glu Leu Leu Ser Glu Thr Ile Phe Lys Ser Gly Val Leu Gly Lys Leu
    370                 375                 380
Leu Thr Thr Gln Lys Leu Asp Asp His Asp Ile Glu Gly Ala Ile His
385                 390                 395                 400
Leu Tyr Tyr Asn Ile Ile Ser Gln Pro Cys Leu Val Cys Lys Asn Leu
                405                 410                 415
Thr Asp Val Glu Leu Leu Arg Lys Tyr Thr Leu Leu His Ser Leu Pro
            420                 425                 430
Leu Asp Lys Ser Leu Lys Ile Val Arg Asn Phe Leu Ile Ser Ala Thr
        435                 440                 445
Ala Lys Asp Cys Ser Leu Met Ile Ser Phe Arg Pro Arg Glu Asn Gly
    450                 455                 460
Ser Thr Asp Ser Glu Tyr Asp Ser Val Phe Leu Glu Ser Ala Lys Arg
465                 470                 475                 480
Thr Tyr Glu Tyr Lys Thr Tyr Phe Val Asp Leu Asp Val Lys Pro Leu
                485                 490                 495
Asp Lys Met Val His Tyr Phe Lys Leu Asp Gln Arg Ile Val Asn Ser
            500                 505                 510
Tyr Thr Arg Tyr Gly Glu Val Leu Pro Pro Lys Gly Lys
        515                 520                 525
```

<210> SEQ ID NO 20
<211> LENGTH: 5143
<212> TYPE: DNA
<213> ORGANISM: Zea mays
<220> FEATURE:
<221> NAME/KEY: gene
<222> LOCATION: (0)...(0)
<223> OTHER INFORMATION: Lpa1 cDNA

<400> SEQUENCE: 20

```
cctctctctc ccctcctcga accaggcgca ggcgagcgtc tctgcccgcc cgcctgctgc    60
taccgccaaa acgcctcctt tgttgccatc cgccgatgcc gtaatccgcc gcccaaagct   120
cttccttttt ccctctctct cgcccgcggc cgcactccct gccccagtgc ctgccgtggc   180
gagcccaacc ccaatgcctt ttaaacccct ccccgctccc tcactgatcc ccaccgcctc   240
ccaatgccgc cctccttccc ctccctcccg ctcccggagg ccgttgccgc caccgcccac   300
gccgcgctgc tcgcgctcgc cgcactcctg ctcctcctcc gcgccgcgcg cgcgctcgcc   360
tcccgctgcg cgtcatgcct caaggcgccg ccgccgcgcg ggggccccgc cgtcgtcgtg   420
ggcgacggcg ccggcggcgc cctcgcggcg gcgactgccg gcgcctggca cagggccgtg   480
ctggcgtcct gcgcctacgc cctgctctcg caggtcgccg tgctgagcta cgaggtggcc   540
gtcgccggct cgcgcgtctc ggcgcgggcg ctgctgctgc cggccgtgca ggcggtgtcc   600
tgggccgcgc tgctggcgct cgcgcttcag gcccgcgccg tcggctgggc caggttccct   660
gcgctggtgc ggctctggtg ggtggtctcc ttcgcgctct gcgttgtcat tgcgtacgac   720
gactccaggc gcctgatagg ccagggcgcg cgcgctgtgg attacgcgca catggttgcc   780
aacttcgcgt ccgtgccggc cctgggcttc ctgtgcttgg ttggtgtcat gggttccacc   840
ggtttggaat tggagtttac ggaggatggc aacggcctgc atgagccgct gctgctcggc   900
aggcagcgca gagaggcaga ggaggagctc ggctgtctga gggtcactcc ctacgctgat   960
```

```
gctgggatcc tcagccttgc aacattgtca tggcttagtc cgttgctctc tgttggtgcg    1020
cagcggccac ttgagttggc tgacataccc ttgctggcgc acaaggaccg tgcaaagtca    1080
tgctataagg cgatgagcgc tcactacgag cgccagcggc tagaataccc tggcagggag    1140
ccatcactca catgggcaat actcaagtca ttctggcgag aggccgcggt caatggcaca    1200
tttgctgctg tcaacacgat tgtgtcgtat gttggacctt acttgatcag ctattttgtg    1260
gactacctca gtggcaacat tgcttccccc catgaaggtt acatccttgc ctctatattt    1320
tttgtagcaa aactgcttga gacactcact gcccgacagt ggtacttggg tgtggacatc    1380
atggggatcc atgtcaagtc tggcctcact gccatggtgt ataggaaggg tctccgactg    1440
tcaaacgcct cacggcagag ccacacgagt ggtgagattg tgaattacat ggccgtcgat    1500
gtgcagcgtg tgggggacta tgcatggtat ttccatgaca tctggatgct tcccctgcag    1560
atcattcttg ctctcgccat cctgtacaag aacgtcggga tcgccatggt ttcaacattg    1620
gtagcaactg tgctatcgat cgcagcctct gttcctgtgg caaagctgca ggagcactac    1680
caagataagt taatggcatc aaaagatgag cgcatgcgca agacttcaga gtgcttgaaa    1740
aatatgagga ttttgaagct tcaggcatgg gaggatcggt accggctgca gttggaagag    1800
atgaggaacg tggaatgcag atggcttcgg tgggctctgt actcacaggc tgcagttaca    1860
tttgttttct ggagctcgcc aatctttgtc gcagtcataa cttttgggac ttgcatatta    1920
ctcggtggcc agctcactgc aggaggggtt ctatccgctt tagcaacgtt tcggatcctc    1980
caagagcctc tgaggaactt cccggatctc atctctatga tggcacagac aagggtgtct    2040
ttggaccgtt tgtctcattt tctgcagcaa gaagaactgc cagatgacgc aactataaat    2100
gttccacaaa gtagtacaga taaggcagtc gatattaagg atggcgcatt ctcttggaac    2160
ccatacactc tgaccccctac actttctgat atacacctta gtgtagtgag aggcatgaga    2220
gtagcagtct gtggtgtcat tggttctggt aaatcaagtc tactatcgtc tatactcggg    2280
gagataccca aattatgtgg ccatgtcagg ataagtggca cagcagcgta tgttcctcag    2340
actgcatgga tacagtctgg aaatattgag gagaatattc tgtttggcag tcaaatggat    2400
agacaacgtt acaagagagt cattgcagct tgctgtctta agaaagatct tgagctgctc    2460
cagtacggag atcagactgt tattggtgat agaggcatta atttgagtgg aggtcagaaa    2520
caaagagttc agcttgctag agcactctac caagatgctg atatttattt gcttgatgat    2580
cccttcagtg ctgttgatgc tcatactggg agcgaactgt ttaaggagta tatattgact    2640
gcactagcaa ccaaaacagt aatctatgta acacatcaag ttgaatttct accagctgct    2700
gatctgatat tggttcttaa ggatggccat atcacacaag ctggaaagta tgatgatctt    2760
ctgcaagctg gaactgattt caatgctctg gtttctgctc ataaggaagc tattgaaacc    2820
atggatatat ttgaagattc cgatagtgat acagtttctt ctattcccaa caaagattg    2880 acaccaagta tcagcaatat tgataacctg aaaaataaga tgtgtgaaaa tggacaacca    2940
tctaatacac ggggaattaa ggaaaaaaag aagaagaag agcgtaagaa gaagcgtact    3000
gttcaagagg aggaaaggga acgtggaaaa gtgagctcca aagtttattt gtcatacatg    3060
ggggaagctt acaaaggtac actgatacca ctaattatct tggctcaaac catgttccaa    3120
gttcttcaga ttgcgagcaa ctggtggatg catgggcaa acccacaaac agaaggagat    3180
gctcccaaga cagatagtgt ggtccttctg gttgtttata tgtcccttgc ctttggaagt    3240
tcactatttg tgttcatgag aagccttctt gtggctacgt ttggtttagc agctgcccag    3300
aagcttttta taaaaatgct taggtgtgtc tttcgagctc caatgtcatt ctttgacacc    3360
```

```
acaccatctg gtcggatttt gaacagagtt tctgtagatc aaagtgttgt ggaccttgat    3420
atagcgttca gacttggtgg atttgcatca acgacaattc aactccttgg aattgttgct    3480
gtcatgagca aagtcacatg gcaagttctg attcttatag tccccatggc tgttgcatgc    3540
atgtggatgc agaggtatta tattgcttca tcaagggaac taactaggat tttgagtgtt    3600
cagaagtctc cagtgatcca tttgtttagt gaatcaattg ctggtgctgc tacaataagg    3660
ggttttggtc aagagaagcg gtttatgaaa aggaatcttt atcttcttga ctgttttgct    3720 cgcccttat tttccagcct tgctgctatt gaatggctct gcctgcgaat ggaattgctt    3780
tcgactttcg tctttgcttt ttgcatggca atacttgtga gctttcctcc tggcacaatc    3840
gaaccaagta tggctggcct cgctgtaaca tatggactta atttaaatgc tcgcatgtca    3900
agatggatat tgagcttctg taaattagag aacaggataa tctctgttga gcgcatttat    3960
caatattgca ggcttcctag tgaagcacca ttgattattg agaactgccg tccaccatca    4020
tcatggcctc agaatggaaa cattgaactg attgatctca aggtccgcta caaggacgat    4080
ctaccattag ttcttcatgg tgtaagttgt atgtttcctg gcgggaaaaa gattgggatt    4140
gtagggcgta ctggaagcgg taaatctact cttattcagg ccctttccg cctaattgag    4200 cccactggag ggaagattat aattgacaac attgacatct ctgcaattgg ccttcatgat    4260
ctgcggtcac ggttgagcat cattccccaa gaccctacat tgtttgaggg tactatcaga    4320
atgaaccttg atcctcttga ggagtgcact gatcaagaaa tttgggaggc actagaaaag    4380
tgtcagctag gagaggtcat tcgttccaag gaagagaaac ttgacagtcc agtgctagaa    4440
aacggggata actggagcgt gggacagcgc caacttattg cactgggtag ggcgctgctc    4500
aagcaggcaa aaattttggt actcgatgag gcgacagcat ctgtcgacac agcaacagac    4560
aatcttatcc aaaagatcat ccgcagtgaa ttcaaggact gcacagtctg taccattgct    4620
caccgtattc ccaccgttat tgacagtgac cttgttctgg tccttagtga tggtaaaatc    4680
gcagagttcg acacgcccca gaggcttta gaggacaagt catctatgtt catacagcta    4740
gtatcggaat actccactcg gtcgagctgt atatagagag gcttagctta aaaccccgcc    4800
ccaaacctgg caacagaggc tgggaggcaa atagcccgta tctgccatgc ttgcgccata    4860
gaggtccctg cgaacaccgg agggcggcgt agaagacgag gtgtacatga gtgggaggaa    4920
cactgggcgt tccctgacct gaataccgtg gaatcggcga gggagcgcgg ttggtattgg    4980
taggcaccag gggaggagtt ggtgacacta gtacattacc cgaagctgat gcttcagtat    5040
gtatgtataa caacaatgca tactgcttct ccctttgcag agtggagaac caagggaata    5100
actcgtgcgt aataagagga gaaagatttg ttttttggca aaa                     5143

<210> SEQ ID NO 21
<211> LENGTH: 1585
<212> TYPE: DNA
<213> ORGANISM: Zea mays
<220> FEATURE:
<221> NAME/KEY: gene
<222> LOCATION: (0)...(0)
<223> OTHER INFORMATION: Lpa3 cDNA

<400> SEQUENCE: 21
gtcgacccac gcgtccgctc gccgccccga gaccccacg cttccctctc cgccccgaa      60 ctgtggcgcc tcccccgcc gccgcagcga tgccactcgc ggcagagccc gacgacgctc     120
atgaggaaag ggagaatcag cagctgctaa ttacgacgaa ggagggccc gggcttgagg     180
```

-continued

```
gactggtggt gggagctac tgccacgatg tgctaatccg gggcgggcgc atagtggggg    240
agacgctcgg cggggctgcg gccttcgtgt ccaacgtgct cgacgccgct tcgccccagg   300
gcgccgcgct caacgagaca tcccccttg tcgttgtggc caaggtgggt cacgacttca    360
tctacgcccg cgcgccggcg tccgcgcggc atccgcctct gctctgctcg tccccaacca   420
cctccttcca cgcccagttc tcggagaccg ccgcctcggc gcacgccccc gaccgggagc   480
tccggcgcgt gcgcgcctgc gacccgatct accccgccga ccttcccgac cgccgcttcg   540
cctacggcct cgctgtcggc gtcgccgggg aggtgctacc ggagacgctc gagcagatga   600
tcaggctctg ccgcacggtg ctcgtggacg cgcaggcgct gatccgggcg ttcgacggtg   660
acggcgccgt cggtcacgtg gcgcttggcg atacccgta cgcgcggctt ctgccccgag    720
tggcgttcgt taaggcgtcg tcggaggagg cgccatacgt tggggtggaa acgacgaggc   780
ggcagtgctg tgtgatcgtc acggagggga gggacggctg ccggctgtac tgggacggtg   840
gggaggcgca cgttgcgccg ttccccgccg tacaggtgga ccctactggc gccggagaca   900
gttttctcgc gggctttgca gccggattgc tgtgggggtt gtcggcgacg gacgccgcgc   960
tgctggggaa cttctttggc gccgctgctg tatcgcaggt cggcgtgccc accttccatc  1020
ccaagatgtt gcaggcagtt aaagaaatac ttgaagagaa gacaaggaaa cgatctagtc  1080
catgtatgaa cggcgctagt tttaccttgg agaagtcaaa tatgcacaac gagttacacg  1140
cagctctcca agaagctgcg gtgctgatgt ctgaacagca gcaggctgat ccggcgaacg  1200
gcagtggcgg tgatatttgc tcggcatagg tacctcacag tgaagctgaa gcagtcgaac  1260
gccaaactga agtttgtggc aaaataacca gcactgcagt cctgaactcc tgatctcaca  1320
ttgagatctg taaacatggt gccaacaagt ggaggaagtt tgtacatacg ctctctccgg  1380
cctttacact actattctgc tggcaaggcc gtcagggatc gtttctacct tgctatcgct  1440
gacgaggaaa tgaagacaac tgaacagttg agctgtggcg cttgcacgca ccatgttttc  1500
tccgctgaac aagtgcgcat ttttgagctt tcgggcattc gtgctgttaa cttttacca   1560
ttctatatgt cgacttctac caaaa                                         1585
```